United States Patent
Nahori et al.

(10) Patent No.: US 8,404,250 B2
(45) Date of Patent: Mar. 26, 2013

(54) GRAM POSITIVE BACTERIA PREPARATIONS FOR THE TREATMENT OF DISEASES COMPRISING AN IMMUNE DYSREGULATION

(75) Inventors: Marie-Anne Nahori, Montrouge (FR); Micheline Lagranderie, Neuilly-sur-seine (FR); Gilles Marchal, Ivry-sur-seine (FR); Bernardo Boris Vargaftig, Paris (FR); Jean Lefort, Clichy-sur-seine (FR); Felix Romain, Fontenay les Briis (FR); Georges Hekimian, Garches (FR); Philippe Peltre, Neuilly-sur-seine (FR)

(73) Assignees: Institut Pasteur, Paris (FR); Institut National de la Sante et de la Recherche Medicale, Paris (FR)

( * ) Notice: Subject to any disclaimer, the term of this patent is extended or adjusted under 35 U.S.C. 154(b) by 380 days.

(21) Appl. No.: 12/582,834

(22) Filed: Oct. 21, 2009

(65) Prior Publication Data
US 2010/0272756 A1  Oct. 28, 2010

Related U.S. Application Data

(60) Division of application No. 11/600,907, filed on Nov. 17, 2006, now Pat. No. 7,871,627, which is a continuation of application No. 10/497,703, filed as application No. PCT/IB02/05760 on Dec. 11, 2002.

(30) Foreign Application Priority Data

Dec. 11, 2001 (EP) .................................. 01403195

(51) Int. Cl.
*A61K 39/04* (2006.01)
(52) U.S. Cl. .................................. 424/248.1
(58) Field of Classification Search .................. None
See application file for complete search history.

(56) References Cited

U.S. PATENT DOCUMENTS

| | | | |
|---|---|---|---|
| 3,594,471 | A | 7/1971 | Hertzberger et al. |
| 4,443,548 | A | 4/1984 | Oshima et al. |
| 4,724,144 | A | 2/1988 | Rook et al. |
| 2007/0190076 | A1 | 8/2007 | Nahori et al. |

FOREIGN PATENT DOCUMENTS

| | | |
|---|---|---|
| GB | 764718 | 1/1957 |
| GB | 1027979 | 5/1966 |
| JP | 63-126830 | 5/1988 |
| WO | WO 86/06634 | 11/1986 |
| WO | 9938529 | 8/1999 |
| WO | WO 00/74715 A1 | 12/2000 |

OTHER PUBLICATIONS

Heydenreich et al. (Clin. Exp. Allergy, doi: 10.1111/j.1365-2222.2011.03888.x, 2011).*
Mao Xiao-Quan, et al., "Th1/Th2 balance control and allergy—The breakdown of Th1/Th2 balance and increase of allergic population", Arerugi/Men-eki (Allergology & Immunology), vol. 7, No. 6, Jun. 2000, 1 page partial English translation only.
Michio Tsukamura, "A case in which a therapy using killed *Mycobacterium scrofulaceum* vaccine was applied against lung cancer", Igaku to Seibutsugaku (Medicine and Biology), vol. 92, No. 1, 1976, 1 page partial English translation only.
International Search Report for PCT/IB02/05760, 2003.
Kyd, J. M. and A.W. Cripps, "Killed Whole Bacterial Cells, a Mucosal Delivery System for the Induction of Immunity in the Respiratory Tract and Middle Ear: an Overview," Vaccine, vol. 17, No. 13-14, pp. 1775-1781, 1999.
Alexandroff, A.B., et al., "BCG Immunotherapy of Bladder Cancer: 20 Years On," The Lancet, vol. 353, No. 9165, pp. 1689-1694, 1999.
Creticos (Am. J. Managed Care, 6(suppl):S940-S963, 2000.
Scanga, et al., (Drugs, 59:1217-1221, 2000.

* cited by examiner

*Primary Examiner* — Brian J Gangle
(74) *Attorney, Agent, or Firm* — Morgan, Lewis & Bockius LLP

(57) ABSTRACT

This application relates to compositions comprising components prepared from Gram positive bacteria such as Gram positive facultative intracellular bacteria for treatment of disorders comprising an immune dysregulation in humans and animals.

15 Claims, 31 Drawing Sheets

GRAM POSITIVE BACTERIA PREPARATIONS FOR THE TREATMENT OF DISEASES COMPRISING AN IMMUNE DYSREGULATION

The present invention relates to compositions comprising components prepared from Gram positive bacteria such as Gram positive facultative intra-cellular bacteria, for example mycobacteria, for the treatment of disorders comprising an immune dysregulation, in humans and animals. The invention also relates to the preparation of said components and compositions.

Diseases comprising an immune dysregulation, such as a Th1-Th2 imbalance, include different cancers, autoimmune diseases such as multiple sclerosis, rhumatoid arthritis, Crohn disease and diabetes mellitus, and allergic disorders such as asthma, allergic rhinitis, conjunctivas and atopic dermatitis.

For instance:

Allergic asthma is a common disease, which involves airway allergen-induced inflammation; the inflammatory leukocytes, eosinophils and sometimes neutrophils, are recruited to airways as a consequence of the presence and activation of T lymphocytes that react with the inhaled allergens in the respiratory tract. CD4+ T lymphocytes play a major role in initiating allergic airways inflammation via the production of Th2-type cytokines, which trigger the recruitment of eosinophils to the airways and possibly their subsequent activation. It has been proposed that an imbalance between Th2 and Th1 effectors drives the pathogenesis of asthma.

Therefore, it has been proposed to stimulate a Th1 immune response in the lungs, for instance by nebulization of IFN-γ or by administration of a mycobacterial vaccine; such a stimulation seems to inhibit the development of secondary allergic processes in mice.

More specifically, extrinsic asthma or atopic asthma (e.g. occupational and drug-induced) is associated with the enhancement of a Th2 type immune response with the production of specific immunoglobulin E (IgE), positive skin tests to common aeroallergens and/or atopic symptoms. The airflow obstruction in extrinsic asthma involves a non-specific bronchial hyperresponsiveness (BHR) caused by inflammation of the airways. This inflammation is mediated by chemicals released by a variety of inflammatory cells including mast cells, eosinophils and lymphocytes. The actions of these mediators result in vascular permeability, mucus secretion and bronchial smooth muscle constriction. In atopic asthma, the immune response producing airway inflammation is brought about by Th2 class of T cells which secrete IL-4 and IL-5. Intrinsic or cryptogenic asthma is reported to develop after upper respiratory tract infections, but can arise de novo in middle-aged or older people, in whom it is more difficult to treat than extrinsic asthma.

Therefore allergic disorders are mediated by T lymphocytes secreting T helper 2 (Th2) cytokines, IL-4, IL-5 and IL-13, resulting in high levels of serum IgE and recruitment of eosinophils. However, Th1 cells may also participate in these pathologies; for instance, Th1 Cells have been identified in chronic atopic skin lesions. Such a Th1-Th2 imbalance has also been found in other disorders such as some cancers, especially bladder cancer or in autoimmune diseases.

Epidemiological studies; for instance those performed by Shirakawa and coll. (Science, 1997, 275, 3), demonstrated an inverse association between tuberculin response and atopic disorders. Such results indicate that previous immunization against certain living Gram positive bacteria such as Gram positive facultative intracellular bacteria, for example mycobacteria such as *M. tuberculosis, M. bovis* or BCG, can protect against atopic diseases.

One of the treatment strategies is to down regulate the Th2 component by inducing a T helper 1 (Th1) response to the relevant allergen or antigen, because Th1 and Th2 cytokines are thought to be mutually antagonistic.

Experimental results from different groups have shown that the immunisation of adult mice with intracellular bacteria including mycobacteria and *listeria*, known to induce a strong Th1 immune response, may counterbalance the allergen or antigen induced Th2 response; in allergy, for instance, it may reduce eosinophilia and the associated BHR.

It is the reason why certain mycobacteria have been proposed for treating allergic disorders and more specifically asthma.

In this respect, different kind of compositions including mycobacteria have been tested:

live BCG vaccines have been considered as having a potential effect in experimental asthma or equivalent, specially when given intranasally (K J. Erb and coll., J. Exp. Med, 1998, 187, 561-569; M A. Nahori and coll., Vaccine, 2001, 19, 1484-1495). However, despite their utility to prevent tuberculosis (J B Milstein and coll., WHO Bull. OMS, 1990, 68, 93-108), live BCG vaccines exhibit several drawbacks; first, they cannot be given to immuno-compromised subjects due to their residual virulence; second, there is a local reaction to intradermal BCG vaccination which is proportional to the total bacterial mass and can lead to local ulceration, or in the case of accidental subcutaneous injection, to more severe reactions (abscess). Therefore, such a vaccine, especially if it was given by the intranasal or aerosol route, would not be adapted for repeated administration over a significant period for the immunotherapy of allergic disorders of the respiratory tract, or other disorders involving a Th1-Th2 imbalance. Administration intranasally or by aerosol could lead to inadmissible adverse effects of the live BCG vaccine in the lungs;

heat-killed preparations of mycobacteria:

heat-killed preparations of BCG or of *Mycobacterium tuberculosis* do not have systematic protective properties when employed in vaccines (R. Janssen and coll., *Immunol.*, 2001, 102, 4, 441-449; M A Skinner and coll., *Immunol.*, 2001, 102, 2, 225-233; G A Rook and coll., Novartis Found Symposium, 1998, 217, 73-87 and 87-93). Moreover, said preparations induce a delayed type hypersensitivity to BCG purified protein derivatives (PPD) that interferes with the diagnosis of tuberculosis. However, it must be noted that some authors have considered that pre-immunization in the newborn period with heat-killed *M. bovis* alone or in addition to *M. vaccae* may potentially be helpful in down-regulating an IgE response (F. Tukenmez and coll., *Pediatr. Allergy Immunol.*, 1999, 10, 2, 107-111; F. Tukenmez and coll., J. Asthma, 2000, 37, 4, 329-334; Nahori and coll., precited);

heat-killed preparations of *Mycobacterium vaccae*, (C C Wang and coll., *Immunol.* 1998, 93, 3, 307-313; WO 00/74715) have clinical application in the immunotherapy of allergy. Some results demonstrate the potency of heat-killed mycobacteria as Th1 adjuvants and show a potential application for recombinant mycobacteria in antigen-specific immune modulation (R. Janssen and coll., *Immunol.*, 2001, 102, 4, 441-449; M A Skinner and coll., *Immunol.*, 2001, 102, 2, 225-233; C C Wang and coll., *Immunol.* 1998, 93, 3, 307-313; WO 00/74715).

Even though, said preparations are active in immunotherapy, they present several drawbacks, shared with the heat-killed preparations of BCG or of *Mycobacterium tuberculosis*, which also preclude their use in immunotherapy.

Indeed, all the heat-killed preparations of mycobacteria:

induce the production of TNF-α by alveolar macrophages, which behaves as a toxic and necrotizing substance, this precluding the use of such heat-killed preparations in immunotherapy, and induce local side effects (P M Shirtcliffe and coll., Am. J. Respir. Crit. Care Med., 2001, 163, 1410-1414), such as itch blistering, induration and necrosis with persisting scares observed in human clinical trials.

Therefore, there is a need for efficient compositions derived from Gram positive bacteria such as Gram positive facultative intracellular bacteria, for example mycobacteria, for the treatment of diseases comprising an immune dysregulation such as a Th1-Th2 imbalance, for example allergic disorders, said compositions being well-tolerated and not having the drawbacks exposed here above.

Furthermore such composition must allow the identification of the active components present in the preparation. The heat-killed preparations which include heating at 120° C. during 10 to 30 minutes would never allow identification of heat labile components.

Accordingly it is one object of the present invention to provide a novel killed Gram positive bacterial preparation such as killed Gram positive facultative intracellular bacterial preparation, for example a killed mycobacterial preparation and compositions containing it, useful in the treatment of diseases comprising an immune dysregulation such as a Th1-Th2 imbalance, for example cancer, autoimmune diseases and allergic disorders without important adverse reactions.

It is another object of the present invention to provide a method of preparing said killed Gram positive bacterial preparation which besides its capacity for the treatment of diseases including immune dysregulation, also preserves the structure of the molecules from the bacteria cells in order to allow the identification of the active molecules from these bacterial cells.

Surprisingly, the Inventors have shown that Gram positive bacteria such as Gram positive facultative intracellular bacteria, for example mycobacteria which are killed by "soft methods" which do not denature the molecules from the bacteria cells are able to stimulate leukocytic regulatory cells (CD4+ CD25+ T cells and/or B cells and/or dendritic cells) in vivo when they are administered to subjects suffering from asthma, or other immune dysregulation. The stimulation of these regulatory cells produces a reshaping of the immune reactivity of the asthmatic subjects which has a local and a systemic effect for a prolonged period (several weeks); as a result, the allergic subjects treated with these killed Gram positive intracellular bacterial preparations are protected from asthma for a prolonged period.

The Inventors have also shown that these killed bacterial preparations wherein the structure of the molecules from the bacteria cells is preserved, do not induce adverse effects such as inflammation, anemia, thrombopenia and induction of TNF-α production.

The present invention relates to a bacterial preparation, characterized in that:

it contains killed Gram positive bacteria, obtainable by a process which does not denature the structure of the molecules from the bacteria cells, and it is able to induce, in vivo, a modulation of the immune response against an antigen (immunomodulatory preparation).

Immunomodulatory preparation means a preparation which is able to modify the ratio between immune regulatory and immune helper cells before or after the induction of an immune response against any antigen (self antigen or foreign antigen). Immune regulatory cells include leukocytic regulatory cells such as CD4+ CD25+ T cells and/or B cells and/or dendritic cells. For example, CD4+ CD25+ T cells are described in Schevach et al., *Nat. Rev. Immunol.*, 2002, 2, 389-400.

According to an advantageous embodiment of said bacterial preparation, it contains killed Gram positive facultative intracellular bacteria.

Gram positive facultative intracellular bacteria means Gram positive bacteria with the capacity of growing in synthetic medium in vitro as well as of infecting eukaryotic cells from a mammalian or non-mammalian host, in vivo and multiplying in those cells, for example macrophages.

According to an advantageous embodiment of said bacterial preparation, it contains killed Gram positive facultative intracellular bacteria chosen from *Listeria* sp., *Corynobacterium* sp., and Actinomycetes comprising *Mycobacteria* sp., *Nocardia* sp. and *Rhodococcus* sp.

Preferably said bacterial preparation contains *Mycobacteria bovis*, more preferably *Mycobacteria bovis* BCG.

A process which does not denature the structure of the molecules from the bacteria cells means a process which results in no extensive denaturation of the spatial configuration of the molecules; preferably, said process preserves the three-dimensional structure of the macromolecules from the bacteria cells such as proteins, polysaccharides and lipids.

These processes which are denominated "soft processes" include with no limitation the use of physical means which disrupt the bacteria cell membranes while preserving the structure of its macromolecular components. These processes include with no limitation: extended freeze-drying, grinding in the presence of silica or zirconium beads, use of the so-called "French press", sonication and gamma-rays irradiation. Other processes which may be used for obtaining the killed bacterial preparation as defined above are known to those of ordinary skill in the art.

For example, extended freeze-dried killed bacterial preparation means that essentially all the water has been removed from said preparation; thus, the extended freeze-dried killed bacterial preparation contains less than 1.5% of residual water, preferably less than 1% and more preferably less than 0.5%. However, in non-optimal freeze-drying conditions, when the preparations of freeze-dried bacteria contain more residual water (about 10%), i.e. all the bacteria are not killed, killing of the residual living bacteria is alternatively obtained by contacting said preparations with air (atmospheric pressure); such preparations have the same properties and activity as the above described extended freeze-dried killed bacterial preparations. The residual water in the extended freeze-dried killed bacterial preparation is for instance determined by the coulometric method of Karl Fisher.

The absence of denaturation of the molecules from the killed Gram positive bacterial preparation according to the invention are verified by any method well-known in the art. For example, the structure of the proteins can be verified by gel electrophoresis of the killed Gram positive bacterial preparation extracts, in denaturing and non-denaturing conditions according to Laemmli, *Nature*, 1970, 277, 680-, by comparison with protein extracts obtained from living bacteria; the proteins are visualised either directly, by staining of the gel with an appropriate dye or after transfer of the proteins onto membranes and staining with appropriate antibodies directed to the Gram positive bacteria proteins. Other methods such as gel filtration or mass spectrometry can also be used to verify the structure of purified molecules from the killed Gram positive bacterial preparation according to the invention.

According to an other advantageous embodiment of said bacterial preparation, it contains extended-freeze-dried killed bacteria obtainable by an extended freeze-drying process.

Preferably, said extended-freeze-dried killed bacterial preparation is prepared by:
 (i) harvesting a culture of live bacteria cells,
 (ii) washing the bacteria cells in water or in an aqueous solution of a salt such as borate,
 (iii) freezing the bacteria cells in water or in an aqueous solution of a salt such as borate,
 iv) killing the frozen bacteria cells by drying them in a lyophiliser, for a time sufficient to remove at least 98.5% of the water, preferably at least 99% and more preferably at least 99.5%, and
 (v) collecting the extended freeze-dried killed bacteria cells.

Alternatively, said extended-freeze-dried killed bacterial preparation is prepared by a process as defined above with the exception that the washing of the bacteria cells in (ii) is omitted.

Preferably, step (iv) is performed at a drying chamber pressure of about 0.02 mBar to 0.2 mBar; more preferably 0.06 mBar to 0.1 mBar, during at least 10 to 12 hours, more preferably over several days with a low heat input and a low cold vapor trap temperature to ensure low temperature of dried killed bacterial preparation throughout the drying (no denaturation of the bacterial cells molecules).

In the freeze-drying process, the extended freeze-drying state is reached when in the absence of air leaks in the freeze-dryer, the vacuum-chamber pressure shows no more variation when the ice condenser and the vacuum pump are separated from the vacuum chamber for some seconds; this means that no more water is capable of being removed from the freeze-dried bacteria (=stable water vapour pressure). For instance, when the cold trap is at −52° C., the pressure in the drying chamber may be in the range of 0.06-0.120 mBar, usually of about 0.09 mBar, for obtaining effectively extended freeze-dried killed bacteria.

The invention relates also to different fractions of the killed bacterial preparation according to the invention, selected in the group consisting of
 a fraction A consisting of an organic solvent extract of said killed bacterial preparation, to eliminate phospholipids,
 a fraction B consisting of a glycosidase-treated extract of said killed bacterial preparation, to eliminate glyco-derived components, such as peptidoglycans,
 a fraction C consisting of a DNase and/or a RNase-digested extract of said killed bacterial preparation, to eliminate nucleic acids,
 a fraction D, consisting of a protease-treated extract of said killed bacterial preparation, to eliminate proteins,
 a fraction E, consisting of a extract of said killed bacterial preparation successively treated by an organic solvent, a glycosidase, a DNase and/or a RNase, and finally a protease.

Preferably:
 said fraction A is obtained by extraction with a methanol/chloroform mixture.
 said fraction B is obtained by digestion with lysozyme.
 said fraction C is obtained by digestion with DNase I and/or RNase A.
 said fraction D is obtained by digestion with subtilisin.

According to an advantageous embodiment of said fractions they are isolated from an extended freeze-dried bacterial preparation, as defined above.

According to an advantageous embodiment of said fractions, they consist of mycobacteria fractions, preferably *Mycobacteria bovis* fractions, more preferably *Mycobacteria bovis* BCG fractions.

The invention also relates to a pharmaceutical composition for the prevention or the treatment of diseases comprising an immune dysregulation such as a Th1-Th2 imbalance, comprising an effective amount of killed bacterial preparation and/or at least one fraction thereof, as defined above, a pharmaceutically acceptable carrier and/or an additive, and/or an adjuvant, and/or an immunostimulant and/or an immunomodulator distinct from the bacterial preparation according to the invention.

Adjuvant means a natural or synthetic product which potentiates the specific immune response to an antigen (antibody production, B and T cell activation) when administered in association with said antigen.

Immunostimulant means a natural or synthetic product which induces a non-specific immune response when administered in association with an antigen (for example an increase of the phagocytosis of the antigen).

According to the invention, said composition may advantageously be used for treating cancers, autoimmune diseases such as multiple sclerosis, rhumatoid arthritis, Crohn disease and diabetes mellitus, and allergic disorders such as asthma, allergic rhinitis and atopic dermatitis.

According to an advantageous embodiment of said composition, it consists of mycobacteria, preferably *Mycobacteria bovis*, more preferably *Mycobacteria bovis* BCG.

According to another advantageous embodiment of said composition, it consists of extended-freeze-dried killed bacteria obtainable by an extended freeze-drying process as defined above; preferably said extended-freeze-dried killed bacteria are obtained by a freeze-drying process as defined above.

According to yet another advantageous embodiment of said composition, it is in a form suitable to be administered by the intranasal route.

According to yet another advantageous embodiment of said composition, it is in a form suitable to be administered by the oral or sublingual routes.

In general, the composition may be administered by parenteral injection (e.g., intradermal, intramuscular, intravenous or subcutaneous), intranasally (e.g. by aspiration or nebulization), orally, sublingually, or topically, through the skin or through the rectum.

As specified, in one embodiment, the composition of the present invention is in a form suitable for delivery to the bronchopulmonary mucosal surfaces. For example, the composition may be suspended in a liquid formulation for delivery to a patient in an aerosol form or by means of a nebuliser device similar to those currently employed in the treatment of asthma.

As specified, in another embodiment, the composition of the present invention is in a form suitable for oral administration. For example, the composition may be in the form of tablets, ordinary capsules, gelatin capsules or syrup for oral administration. These gelatin capsule, ordinary capsule and tablet forms can contain excipients conventionally used in pharmaceutical formulation, such as adjuvants or binders like starches, gums and gelatin, adjuvants like calcium phosphate, disintegrating agents like cornstarch or alginic acids, a lubricant like magnesium stearate, sweeteners or flavourings. Solutions or suspensions can be prepared in aqueous or non-aqueous media by the addition of pharmacologically compatible solvents. These include glycols, polyglycols, propylene glycols, polyglycol ether, DMSO and ethanol.

The composition may additionally contain a pharmaceutically acceptable carrier and/or an additive and/or an immunostimulant and/or an adjuvant such as a liposome containing the bacteria cells or fraction(s) thereof according to the present invention; said one or more additives used for preparing pharmaceutical compositions may be chosen among anti-aggregating agents, antioxidants, dyes, flavor enhancers, or smoothing, assembling or isolating agents, and in general among any excipient conventionally used in the pharmaceutical industry.

While any suitable carrier known to those of ordinary skill in the art may be employed in the pharmaceutical composition of the present invention, the type of carrier will vary depending on the mode of administration. For parenteral administration, such as subcutaneous injection, the carrier preferably comprises water, saline buffer, lactose, glutamate, a fat or a wax. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g. polylactic galactide) may also be employed as carriers for the pharmaceutical compositions of this invention. Suitable biodegradable microspheres are disclosed, for example in U.S. Pat. Nos. 4,897,268 and 5,075,109.

Any of the variety of adjuvants may be employed in the compositions of the present invention to enhance the immune response. Most adjuvants contain a substance designed to protect the antigen from rapid catabolism or to create controlled inflammatory reactions, such as aluminium hydroxide or mineral oil, and a non-specific stimulator of immune response, such as lipid A, *Bordetella pertussis* toxin. Suitable adjuvants are commercially available as, for example, Freund's Incomplete Adjuvant and Freund's complete adjuvant which can not be used for injection in human. Other suitable adjuvants which can be used in human include aluminium hydroxide, biodegradable microspheres, monophosphoryl A and Quil A.

The preferred frequency of administration and effective dosage will vary from one species and one subject to another. For example, the amount of extended freeze-dried killed mycobacterial preparation or fraction(s) thereof, is in a dose ranges which is equivalent in mice to about 1 µg to 10000 µg material (approximately $10^6$ to $10^{10}$ CPU); preferably from 10 µg to about 1000 µg; more preferably from about 10 µg to 100 µg. The doses may be higher or lower, depending on the body surface of the species or the subjects and on the frequency of administration. For example, the administration of one or two doses once every two months may be more efficient in the treatment of asthma.

The invention also relates to products containing a bacterial preparation according to the invention or fractions thereof and a product selected from the group consisting of anticancer, anti-diabetes and immunomodulatory drugs, as a combined preparation for simultaneous, separate or sequential use in the prevention and/or the treatment of diseases comprising an immune dysregulation.

Preferably, said products are chosen from anti-histaminic and anti-inflammatory drugs.

The invention also relates to the use of a bacterial preparation according to the invention or fractions thereof for the preparation of a medicament for the treatment of asthma, to be administered by the oral, sublingual, parenteral or intranasal route, in a dose range which is equivalent in mice to 1 µg to 10 000 µg, preferably 10 µg to 1 000 µg, most preferably 10 µg to 100 µg, at two months intervals, starting from at least two weeks before the usual period of allergen exposure.

The invention also relates to a use of a bacterial preparation according to the invention or fractions thereof for the preparation of a medicament for the prevention of asthma in human baby, to be administered by the oral, sublingual, parenteral or intranasal route, in a dose range which is equivalent in mice to 1 µg to 10 000 µg, preferably 10 µg to 1 000 µg, most preferably 10 µg to 100 µg.

The instant invention also relates to a method for the preparation of said extended freeze-dried killed bacterial preparation, characterized in that it comprises at least the steps of (i) harvesting a culture of live bacteria cells, (ii) washing the bacteria cells in water or in an aqueous salt such as borate, (iii) freezing the bacteria cells in water or in an aqueous salt such as borate, (iv) killing the frozen bacteria cells by drying them in a lyophiliser, for a time sufficient to remove at least 98.5% of the water, preferably at least 99% and more preferably at least 99.5%, and (v) collecting the extended freeze-dried killed bacteria cells.

An alternative method for the preparation of said extended freeze-dried killed bacterial preparation, comprises steps (1), (iii), (iv) and (v); the washing of the bacteria cells in step (ii) is omitted.

Preferably, step (iv) is performed at a drying chamber pressure of about 0.02 mBar to 0.2 mBar; more preferably 0.06 mBar to 0.1 mBar, during at least 10 to 12 hours, in order to remove at least 98.5% of the water while preventing melting of the frozen bacteria and maintaining the dried killed bacteria below the bacterial cells molecules denaturation temperature.

According to a advantageous embodiment of said method, it consists of the preparation of extended freeze-dried killed mycobacteria.

The instant invention also relates to the use of said killed bacteria cells preparation or fraction(s) thereof for the preparation of a medicament for the prevention and/or the treatment of diseases comprising an immune dysregulation such as a Th1-Th2 imbalance, e.g. cancers, autoimmune diseases such as multiple sclerosis, diabetes mellitus and Crohn disease, allergic disorders, such as asthma, allergic rhinitis or atopic dermatitis.

According to said use, said killed bacterial preparation or fraction(s) thereof are associated with a pharmaceutically acceptable carrier, and/or an immunostimulant, and/or an adjuvant and/or any conventional additives as defined hereabove.

According to an advantageous embodiment of the invention mycobacteria, preferably *Mycobacteria bovis*, more preferably *Mycobacteria bovis* BCG are used According to another advantageous embodiment of the invention, extended-freeze-dried killed bacteria obtainable by an extended freeze-drying process are used.

The killed bacterial preparations according to the invention have the following advantages:

- they protect the subjects against diseases comprising an immune dysregulation such as a Th1-Th2 imbalance, e.g. asthma for example,
- they are not infectious and may be administered to immunodeficient subjects,
- they do not lead to inflammatory adverse effects, probably due in particular to the fact that they do not induce the production of TNF-α, which can lead to toxicity and necrotizing activity. In addition, they do not produce other side effects including anemia and thrombopenia,
- they can be used without induction of a delayed type hypersensibility to BCG purified protein derivatives (PPD) and thus do not interfere with the diagnosis of tuberculosis,
- and they are prepared by a method that preserves the structure of the molecules from the bacteria cells (no extensive denaturation of the molecules), and thus allows the identification of the immunomodulatory molecules from said killed bacterial preparations.

The present invention also relates to a kit for the treatment of a disease comprising an immune dysregulation, characterised in that it comprises at least a pharmaceutical composition according to the invention, means of administration of said pharmaceutical composition and/or means for insuring compliance with the prescribed treatment.

The present invention will be further illustrated by the additional description and drawings which follows, which refers to examples illustrating the protective effect of extended freeze-dried killed BCG on asthma in mice, the analysis of the immune response induced by extended freeze-dried killed BCG, heat-killed BCG and living BCG, or of the production of extended freeze-dried killed BCG and fractions thereof. It should be understood however that these examples are given only by way of illustration of the invention and do not constitute in anyway a limitation thereof.

FIG. 1 illustrates the standard method of preparation of freeze-dried living BCG vaccine (A) by comparison with the method of preparation of extended freeze-dried killed BCG according to the present invention (B): the pressure in mBar (-Δ-) and the temperature in degree Celsius of the samples (-○-) or of the trays (-●-) are indicated over the time in hours.

FIG. 2 illustrates the protective effect of extended freeze-dried killed BCG (Lyoph killed BCG) on broncho-pulmonary hyper-reactivity in a particularly stringent (highly Th2) BP2 mice model of asthma as assayed by the reduction in ventilation. The BP2 strain of mice is highly responsive along the Th2/asthma axis. The mice are also sensitized with OVA in combination with alum, known to be a Th2 stimulant. By comparison, in this stringent mice model, no significant effect is observed in the groups treated with living BCG or heat-killed BCG. The area under the curve ($cm^2$) is presented: individual (-○-), mean SEM per group of mice (-●-).

FIG. 3 illustrates the protective effect of extended freeze-dried killed BCG (Lyoph killed BCG) on broncho-pulmonary hyper-reactivity in the BP2 mice model of asthma using OVA as allergen, as assayed by broncho-pulmonary resistance. By comparison, no significant effect is observed in the groups treated with living BCG or heat-killed BCG. Enhanced pause (Penh) measured at 1 minute interval are presented: individual data (-○-), mean±SEM per group of mice (-●-). ***Statistically significant ($p<0.001$) protective effect on broncho-pulmonary hyper-reactivity in the extended freeze-dried-killed BCG treated group.

FIG. 4 illustrates the protective effect of extended freeze-dried killed BCG (Lyoph killed BCG) against the increase of eosinophils in the lungs, in the BP2 mice model of asthma, as assessed by cell numeration of the bronchoalveolar lavages (BAL). By comparison, no significant effect is observed in the groups treated with living BCG or heat-killed BCG. Individual data (-○-) and mean±SEM per group of mice (-●-) are presented.

FIG. 5 illustrates the protective effect of extended freeze-dried killed BCG (Lyoph killed BCG) against the increase of neutrophils in the lungs, in the BP2 mice model of asthma, as assessed by cell numeration of the bronchoalveolar lavages. By comparison, no significant effect is observed in the mice treated with living BCG or heat-killed BCG. Individual data (-○-) and mean±SEM per group of mice (-●-) are presented.** Statistically significant reduction of the number of neutrophils ($p<0.01$) in the extended freeze-dried killed BCG treated group.

FIG. 6 illustrates the advantageous absence of lung inflammation or tissue damage, with extended freeze-dried killed BCG (Lyoph killed BCG) in the BP2 mice model of asthma, as assayed by the very low level of fibronectin in bronchoalveolar lavages. By comparison, a significantly higher level of fibronectin in the BAL is observed in the groups treated with living BCG or heat-killed BCG. Data are expressed in IU/ml; individual data (-○-), mean±SEM per group of mice (-●-).*** Statistically significant reduction of the level of fibronectin ($p<0.001$) in the extended freeze-dried killed BCG treated group.

FIGS. 11B (BP2) and 12B (BALE/c) illustrate the absence of production of TNF-α in the macrophages from mice stimulated by extended freeze-dried killed (Lyophilized) compared to significant level of TNF-α produced in the macrophages from mice stimulated by heat-killed BCG (Heated). Data are expressed in or ng/ml per 100 000 cells.

Figure 13:
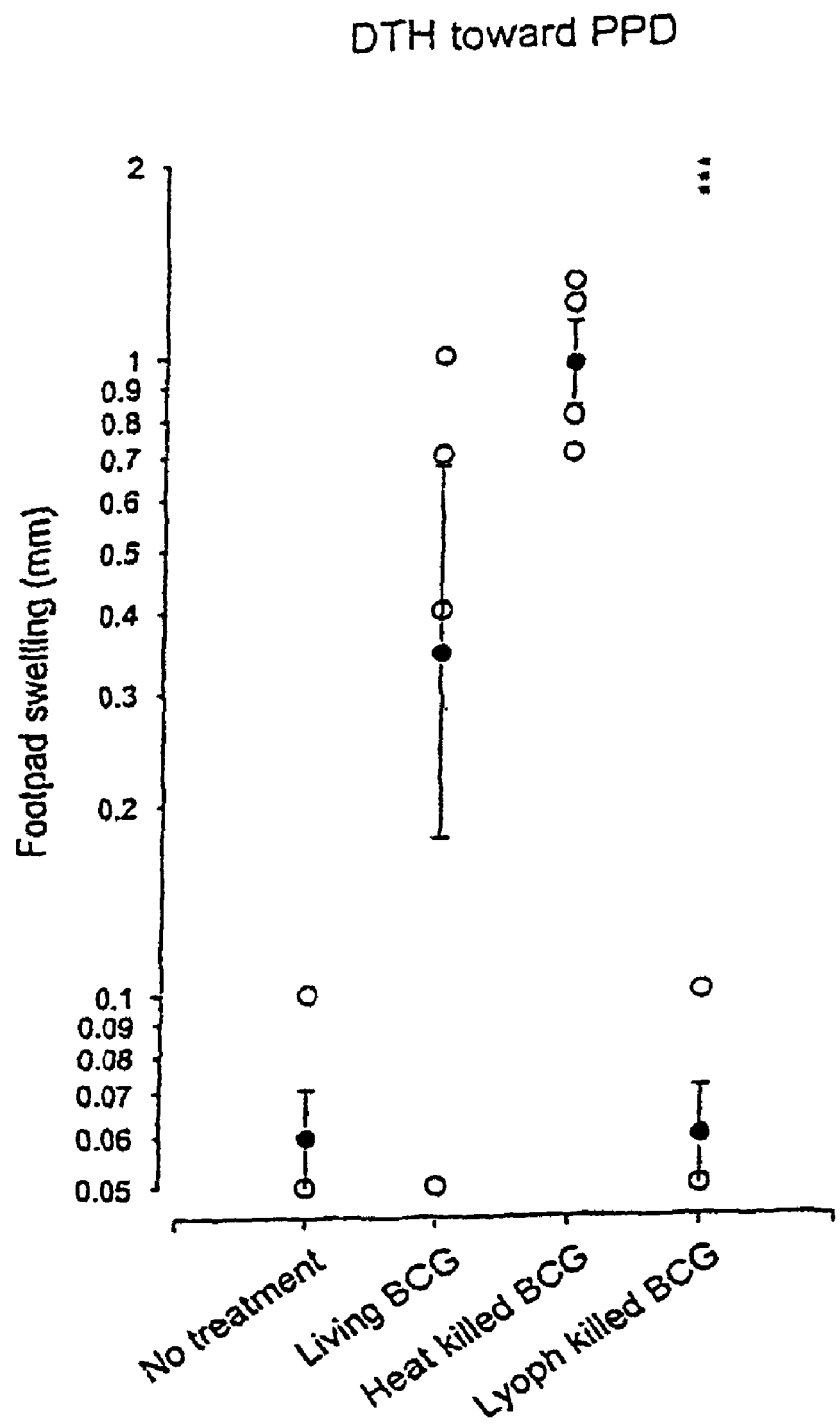

FIG. 13 illustrates the absence of delayed type hypersensitivity (DTH) to BCG purified proteins derivatives (PPD) in mice that have been treated with extended freeze-dried killed BCG (Lyoph killed BCG). By comparison DTH is observed in mice that have been treated either with living BCG or with heat-killed BCG. Individual data (-○-) and mean±SEM per group of mice (-●-) are presented. ***Statistically significant absence of foot-pad swelling (p<0.001) in the extended freeze-dried killed BCG treated group.

Figure 14A:
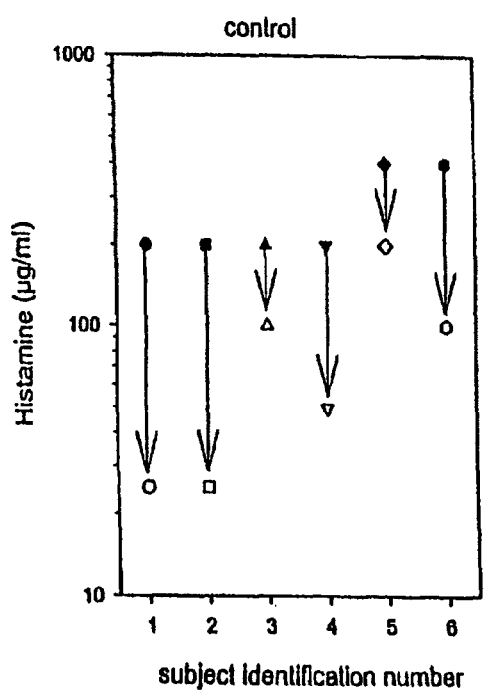
Figure 14B:
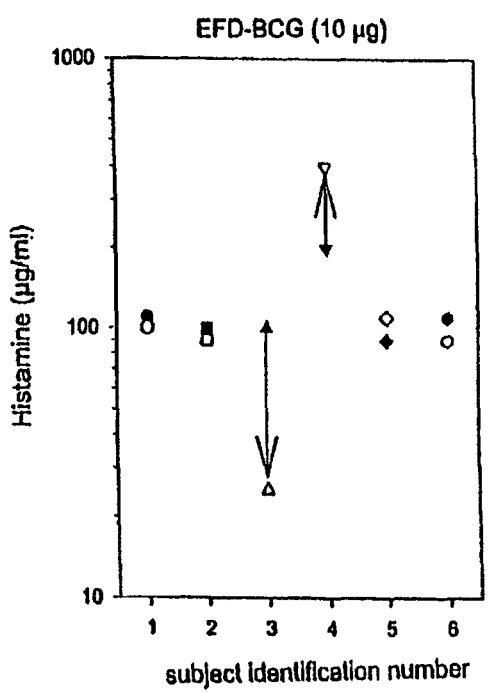
Figure 14C:
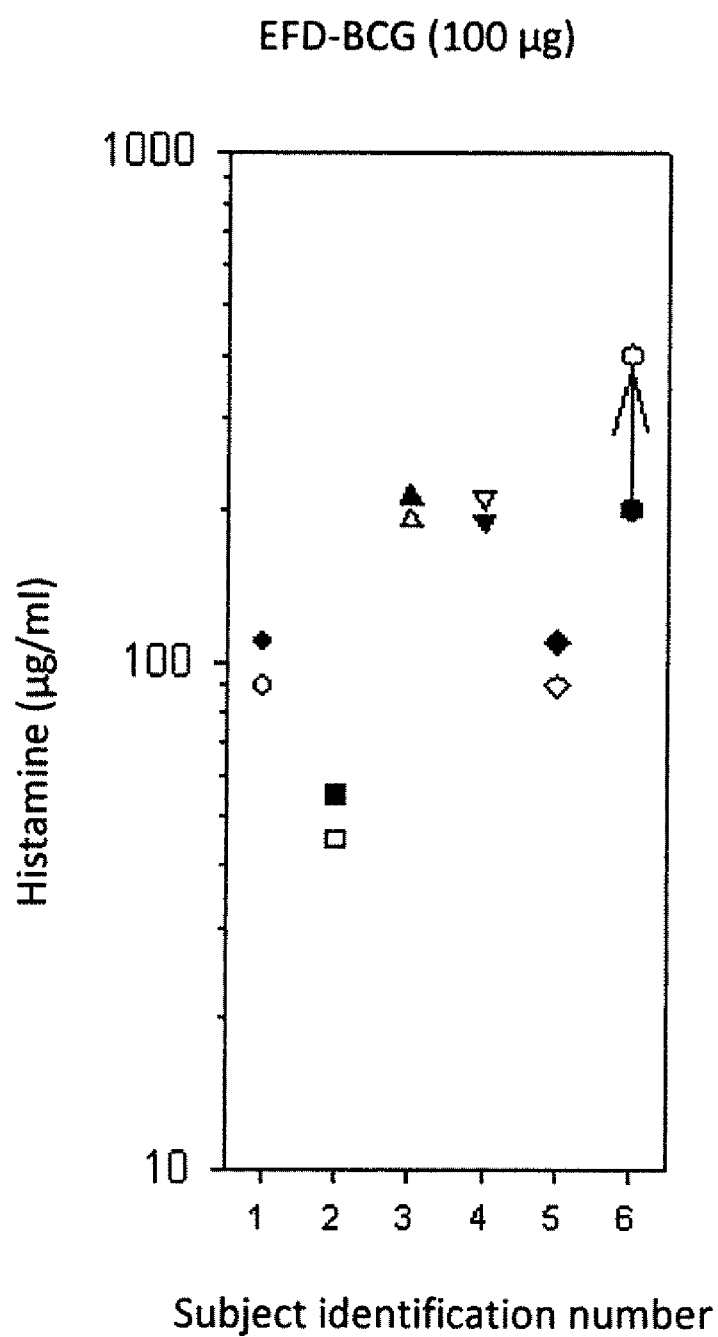

FIG. 14 illustrate the protective effect of extended freeze-dried killed BCG (EFD-BCG) on broncho-pulmonary hyper-reactivity to histamine in a guinea-pig model of asthma. Groups of OVA immunised animals were treated with 10 μg (FIG. 14B) or 100 μg (FIG. 14C) of extended freeze-dried killed BCG, or non-treated (FIG. 14A). Concentration of histamine able to create broncho-constriction before (black symbols) and after (white symbols) aerosol administration of OVA are presented for each animal. ***Statistically significant protective effect in the group treated with 10 μg (p<0.01) or 100 μg (p<0.001) extended freeze-dried killed BCG (Kruskal—Wallis non parametric test).

FIG. 15A illustrates the protective effect of extended freeze-dried killed BCG (EFD1) against the increase of eosinophils in the lungs, in the BP2 mice model of asthma, as assessed by cell numeration of the bronchoalveolar lavages. By comparison, no significant effect is observed in the groups treated with living BCG or heat-killed BCG. The data are expressed as mean±SEM per group of mice; n=7 for each group. *Statistically significant reduction of the number of eosinophils (p<0.05) in the extended freeze-dried killed BCG treated group.

FIG. 15B illustrates the level of IL-5 in bronchoalveolar lavages from groups of mice that have been treated with living BCG, heat-killed BCG, extended freeze-dried killed BCG (EFD1), or non-treated. The data are expressed as mean±SEM per group of mice; n=7 for each group.

Figure 16:
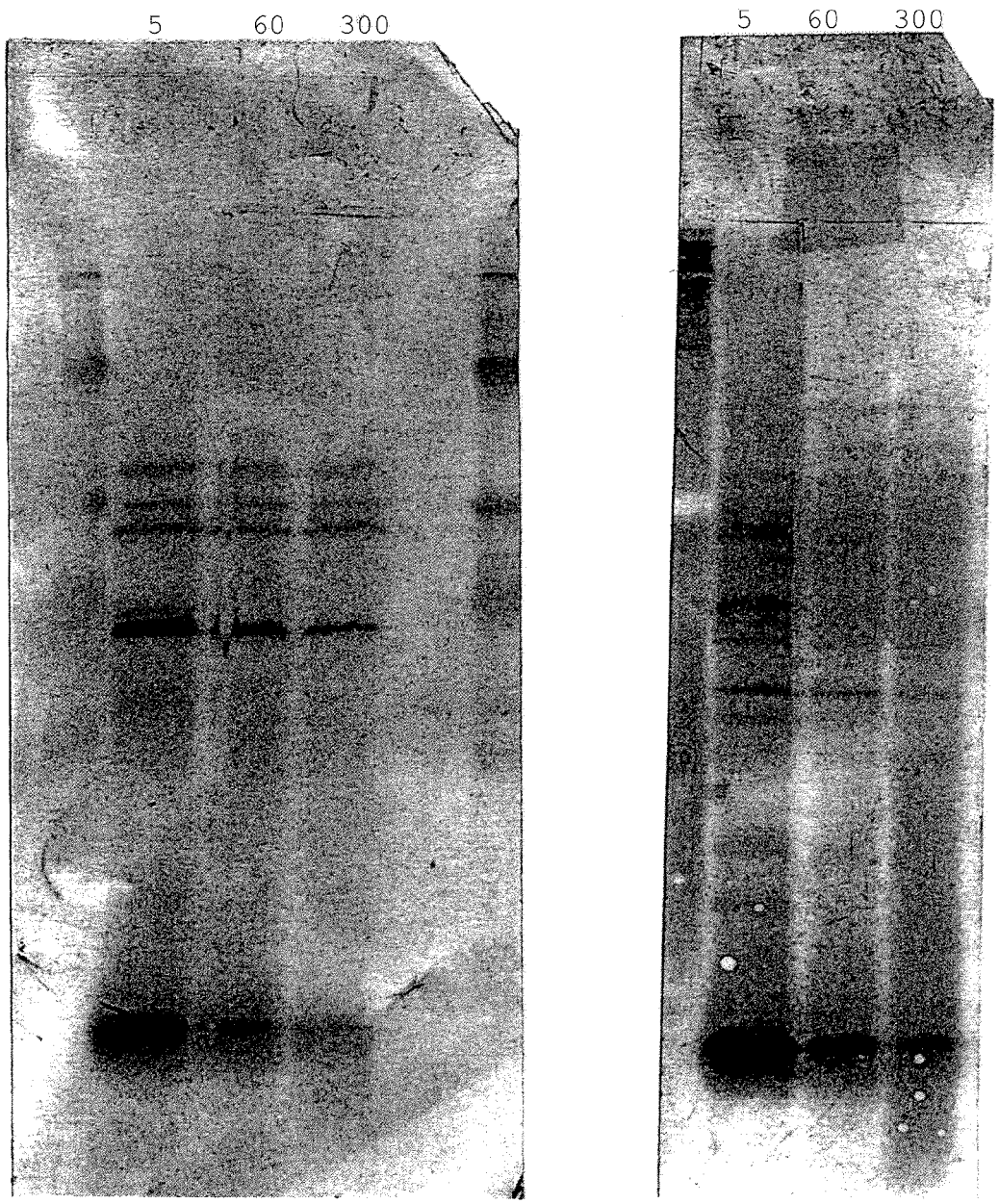

FIG. 16 illustrates the preservation of the structure of the proteins in the extended freeze-dried killed BCG preparations as assessed by SDS-PAGE and (A) staining with anti-mycobacteria antibodies after transfer onto PVDF membranes or (B) staining with Aurodye. The proteins appear as discrete bands without smear.

Figure 17:
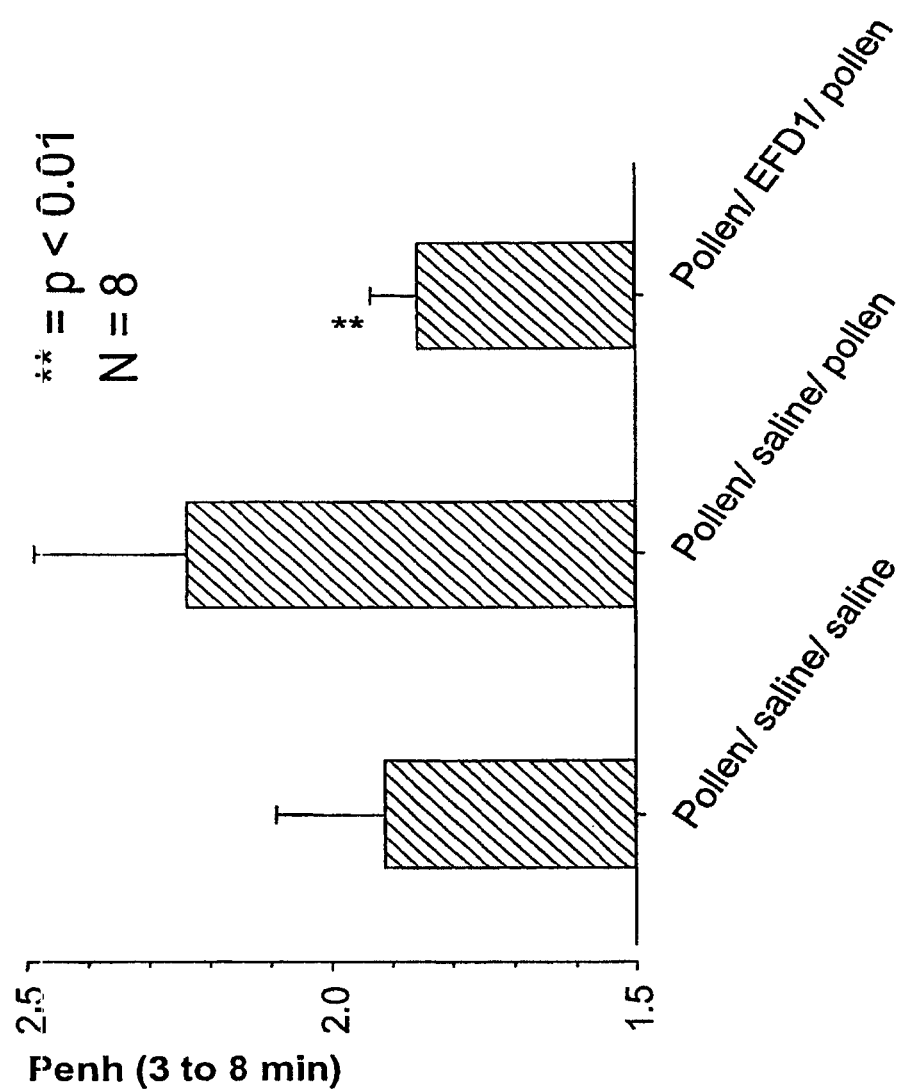

FIG. 17 illustrates the protective effect of extended freeze-dried killed BCG (EFD1) on broncho-pulmonary hyper-reactivity in the BP2 mice model of asthma using a water soluble ray-grass pollen extract as allergen, as assayed by broncho-pulmonary hyper-reactivity. Enhanced pause (Penh) measured between 3 and 8 minutes after methacholine administration are presented: data are presented as mean±SEM per group of mice; n=8 for each group. **Statistically significant (p<0.01) protective effect on broncho-pulmonary hyper-reactivity in the extended freeze-dried-killed BCG treated group.

Figure 18:
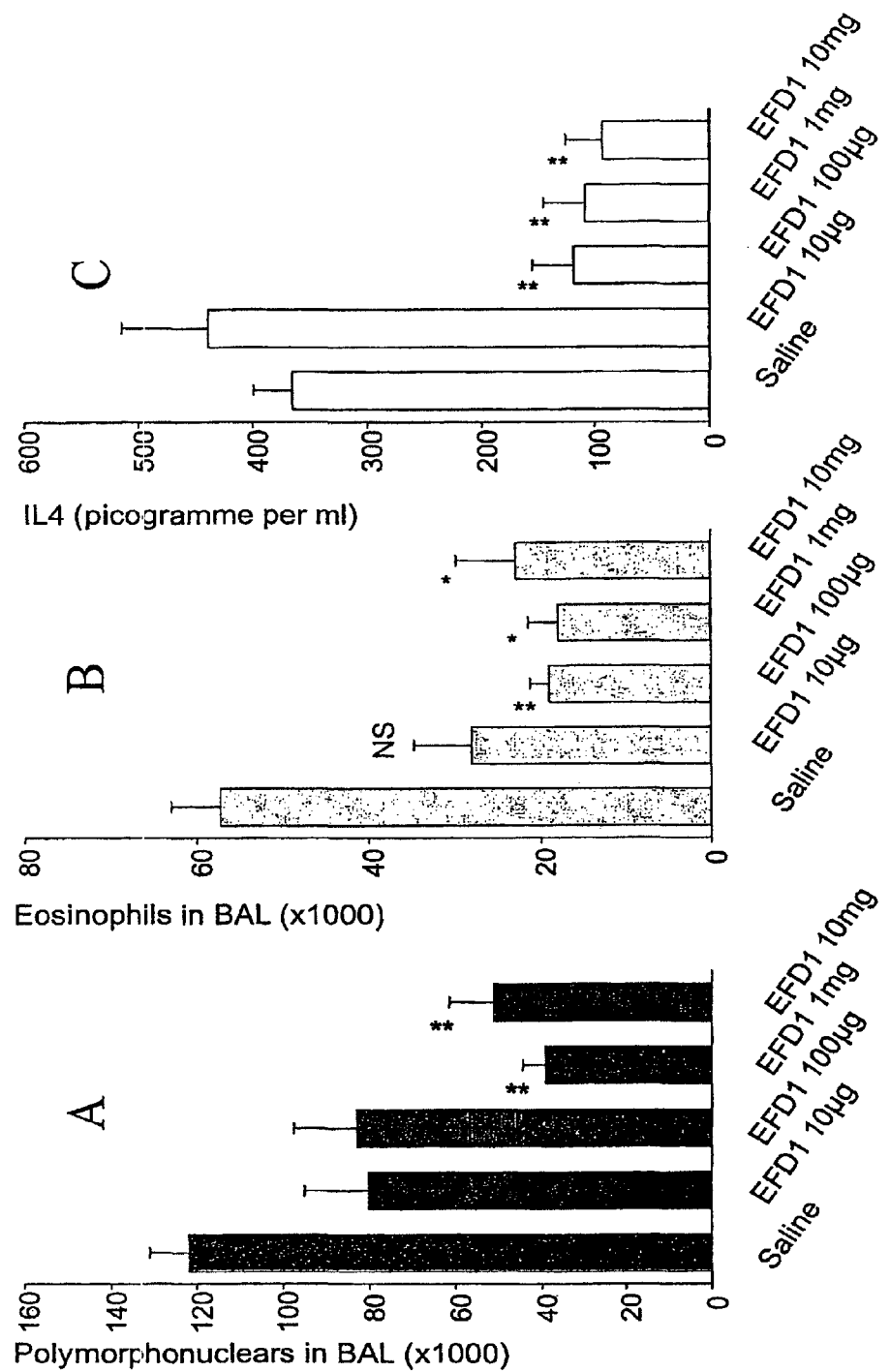

FIGS. 18A and B illustrates the protective effect of extended freeze-dried killed BCG (EFD1) against the increase of polymorphonuclears and eosinophils in the lungs, in the BP2 mice model of asthma, as assayed by cell numeration of the bronchoalveolar lavages. The data are expressed as mean SEM per, group of mice. Statistically significant reduction of polymorphonuclears number (p<0.01) in the groups treated with 1 mg and 10 mg extended freeze-dried killed BCG; statistically significant reduction of the eosinophils number: p<0.01, *p<0.05 and *p<0.05 in the groups treated with respectively 100 μg, 1 mg and 10 mg of extended freeze-dried killed BCG.

FIG. 18C illustrates the correlation between the decrease of the number of polymorphonuclears and eosinophils in the lungs of the extended freeze-dried BCG (EFD1) treated groups (10 μg, 100 μg, 1 mg and 10 mg), and the decrease of IL-4 production as assessed by cells and cytokines analysis in the bronchoalveolar lavages. The data are expressed as mean±SEM per group of mice. Statistically significant reduction of the level of IL-4 (**p<0.01) in the groups treated with 10 μg, 100 μg, 1 mg and 10 mg of extended freeze-dried killed BCG.

Figure 19:
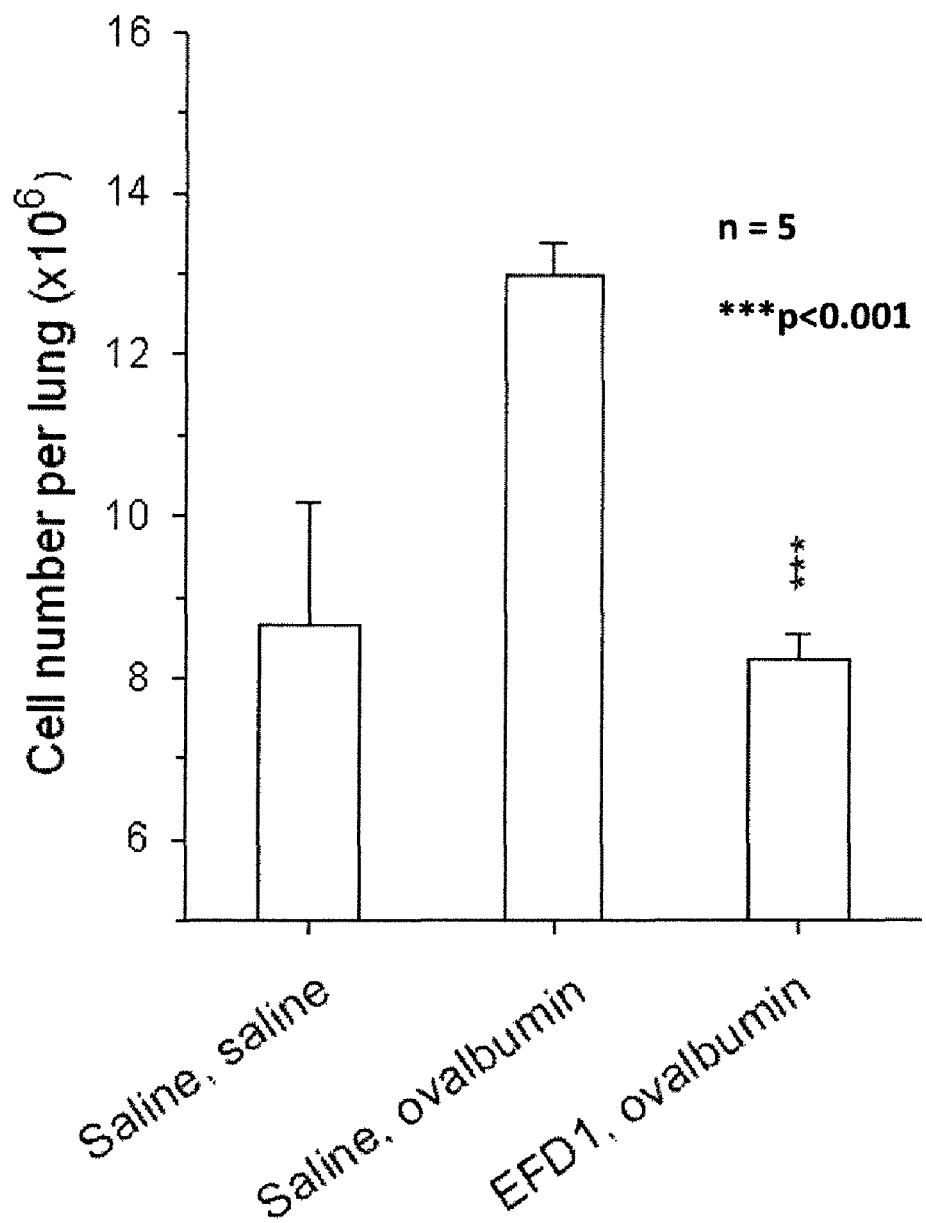

FIG. 19 illustrates the prevention of leukocyte infiltration of the lungs in the extended freeze-dried killed BCG (EFD1) treated groups, in the BP2 mice model of asthma, as assayed by lungs cellular infiltrate numeration. The data are expressed as mean±SEM per group of mice; n=5 for each group. Statistically significant reduction of the number of cells (**p<0.001) in the groups treated with 10 μg extended freeze-dried killed BCG.

Figure 20:
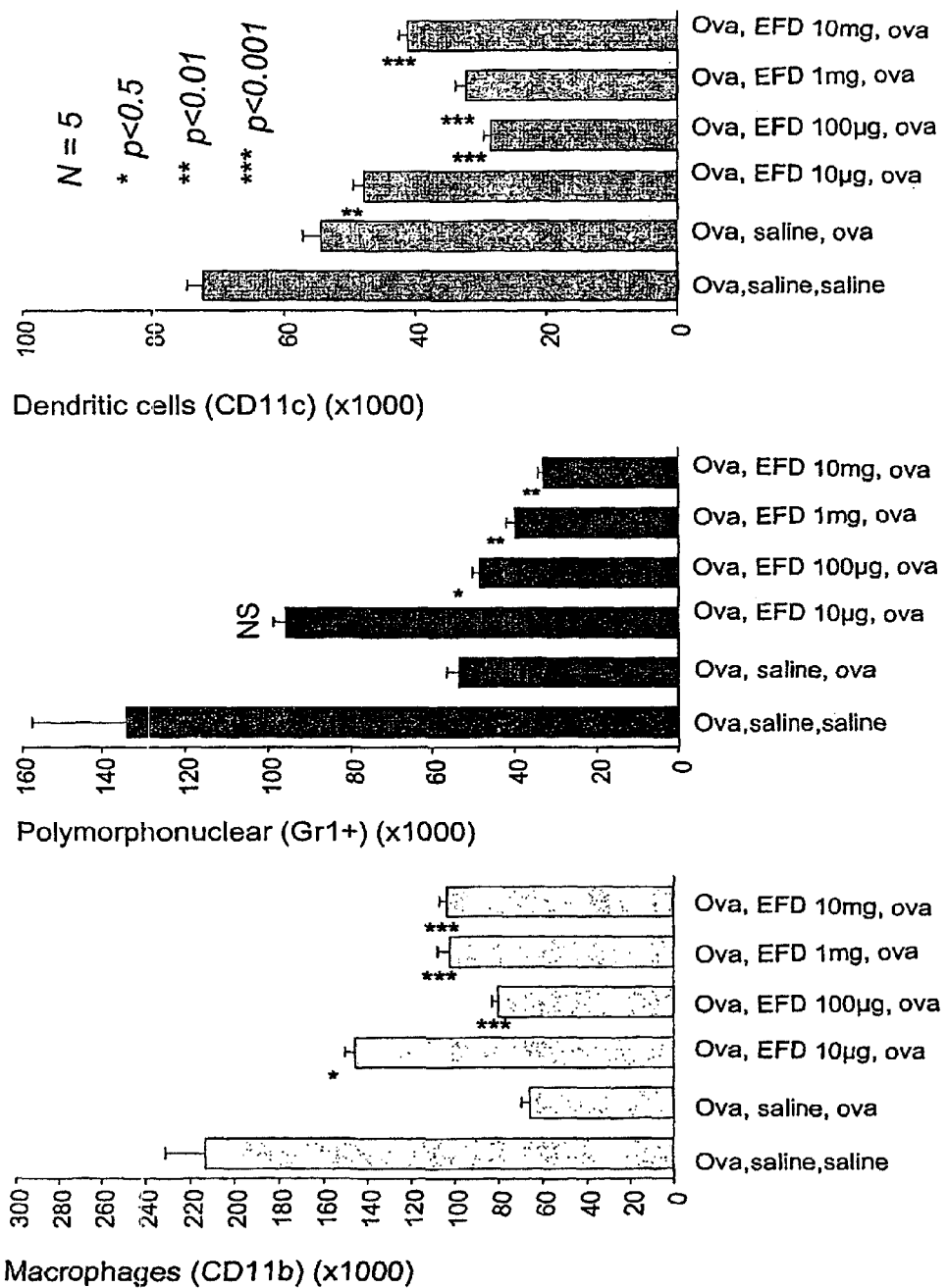

FIG. 20 illustrates the prevention of leukocyte infiltration of the lungs in the extended freeze-dried killed BCG (EFD) treated groups, in the BP2 mice model of asthma, as assayed by flow cytometry analysis of the macrophages (CD11b+), the plymorphonuclear cells (Gr1+) and the dendritic cells (CD11c+). The data are expressed as mean d SEM per group of mice; n=5 for each group. Statistically significant reduction of the number of (i) macrophages and dendritic cells in all the groups treated with extended freeze-dried killed BCG (10 μg 100 μg, 1 mg and 10 mg), and (ii) polymorphonuclears in the groups treated with 100 μg, 1 mg and 10 mg extended freeze-dried killed BCG only.

Figure 21:
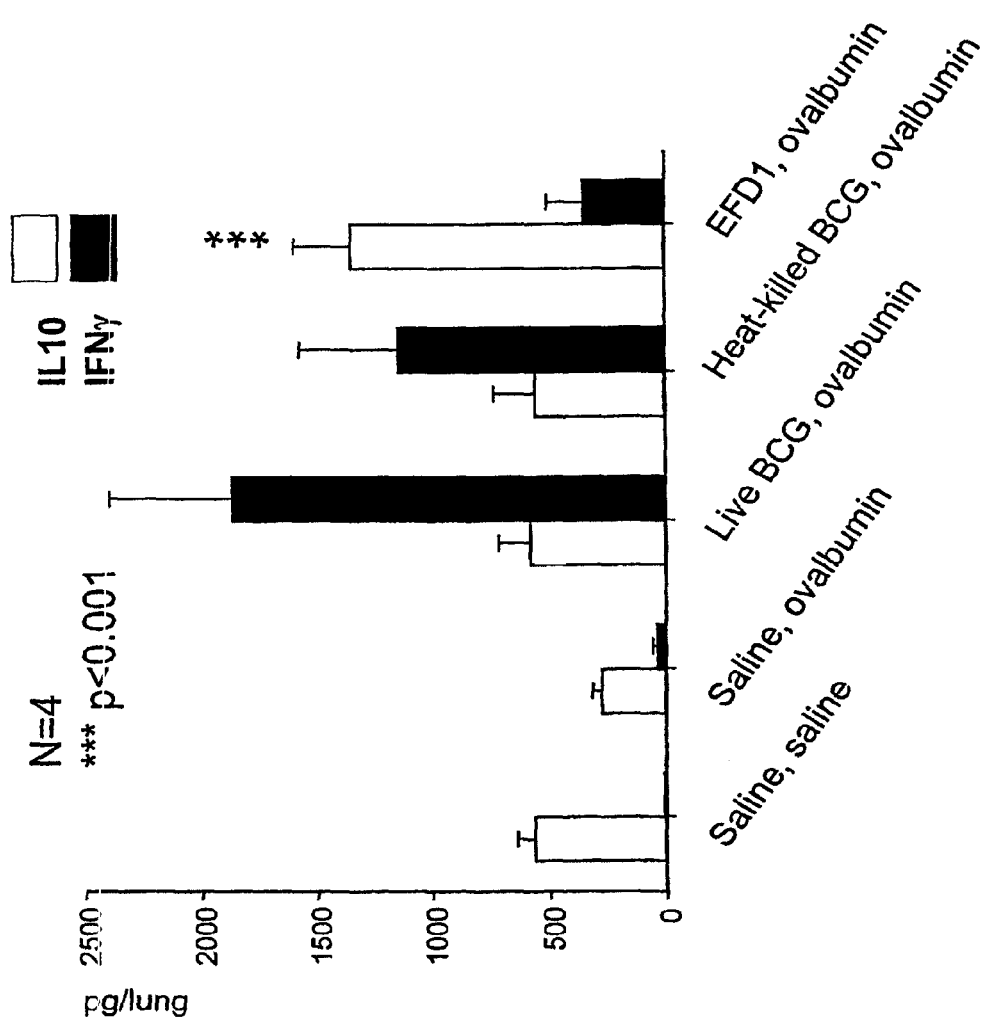

FIG. 21 illustrates the level of IFN-γ and IL-10 (μg/lung) in lung cultures from groups of mice which have been treated with living BCG, heat-killed BCG, extended freeze-dried killed BCG (EFD1) or non-treated and challenged with OVA or not; the cultures have been stimulated in vitro with purified BCG secreted protein Data are expressed as mean±SEM per group of mice; n=4 for each group. Statistically significant increase of IL-10 production (***p<0.001) in the groups treated with extended freeze-dried killed BCG only.

Figure 22:
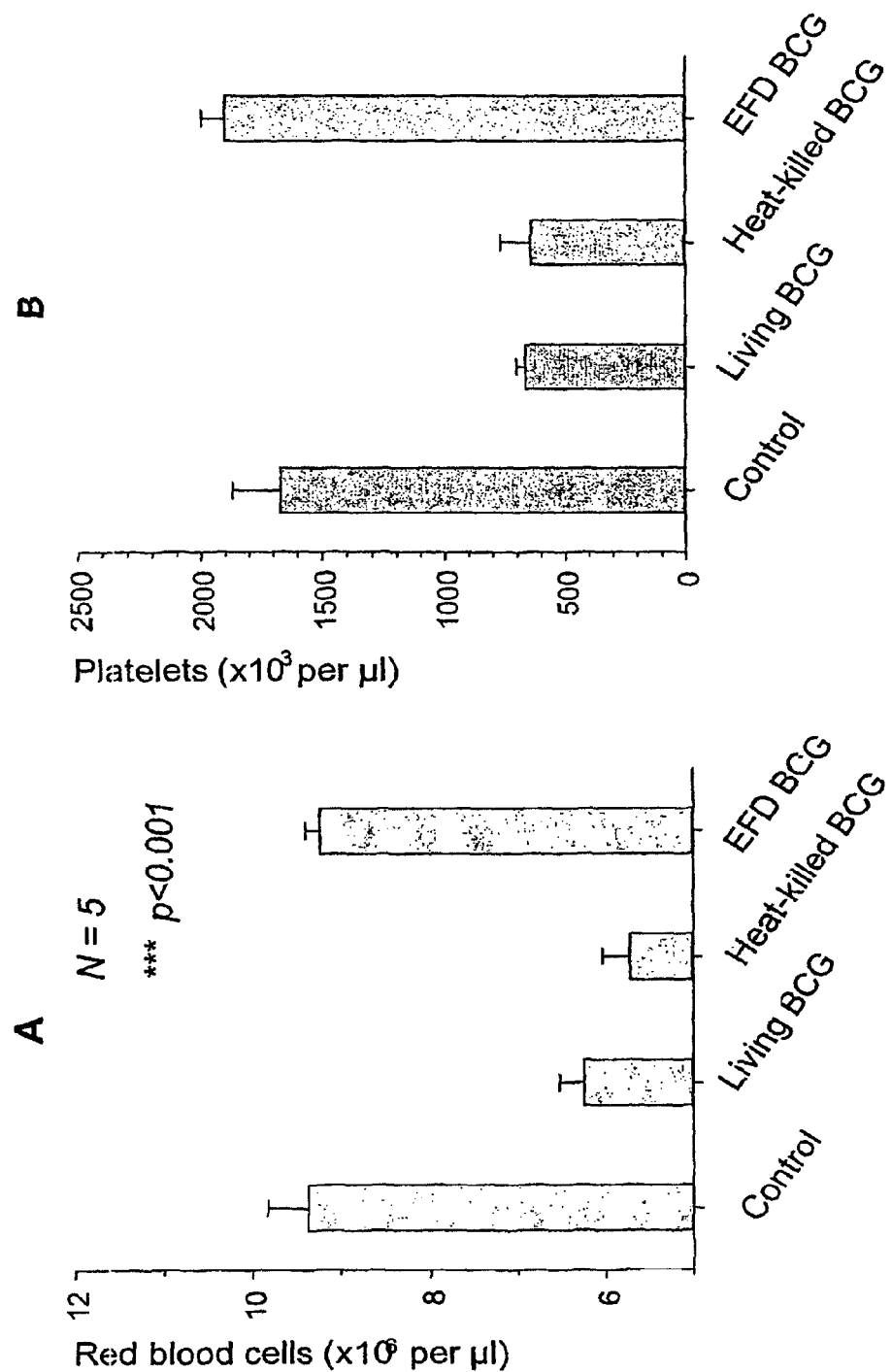

FIG. 22 illustrates the absence of anemia (A) and thrombopenia (B) after intravenous administration of extended freeze-dried killed BCG (EFD-BCG), contrary to administration of living BCG or heat-killed BCG by the same route.

Figure 23:
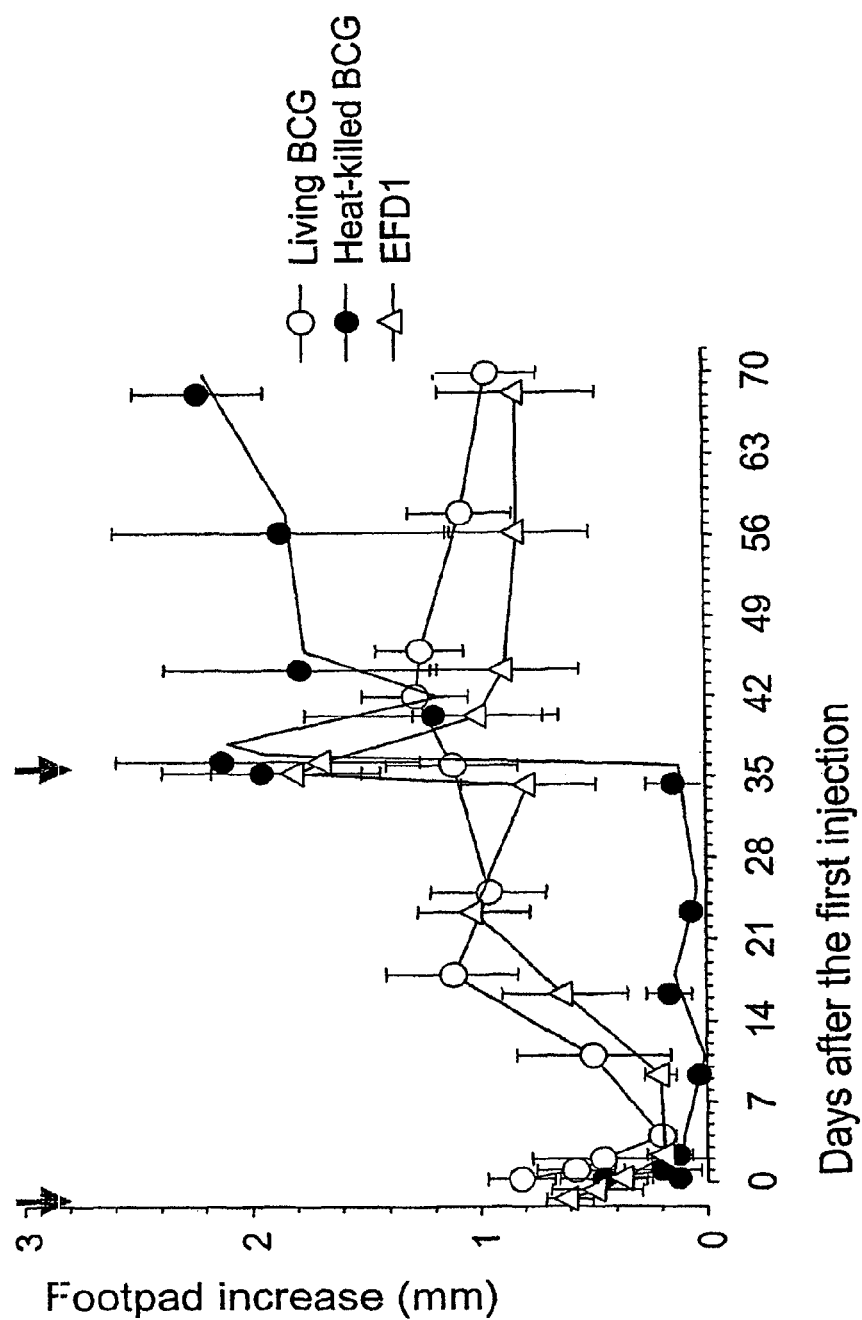

FIG. 23 illustrates the minimal inflammatory reaction at the site of injection after subcutaneous injection of extended freeze-dried killed BCG (EFD1), by comparison with living BCG and heat-killed BCG, as assessed by footpad increase measurement every week for 10 weeks after the injection. Arrow indicate the day of injection; D0 and D36 for EFD and heat-killed BCG, D0 only for living BCG.

Figure 24:
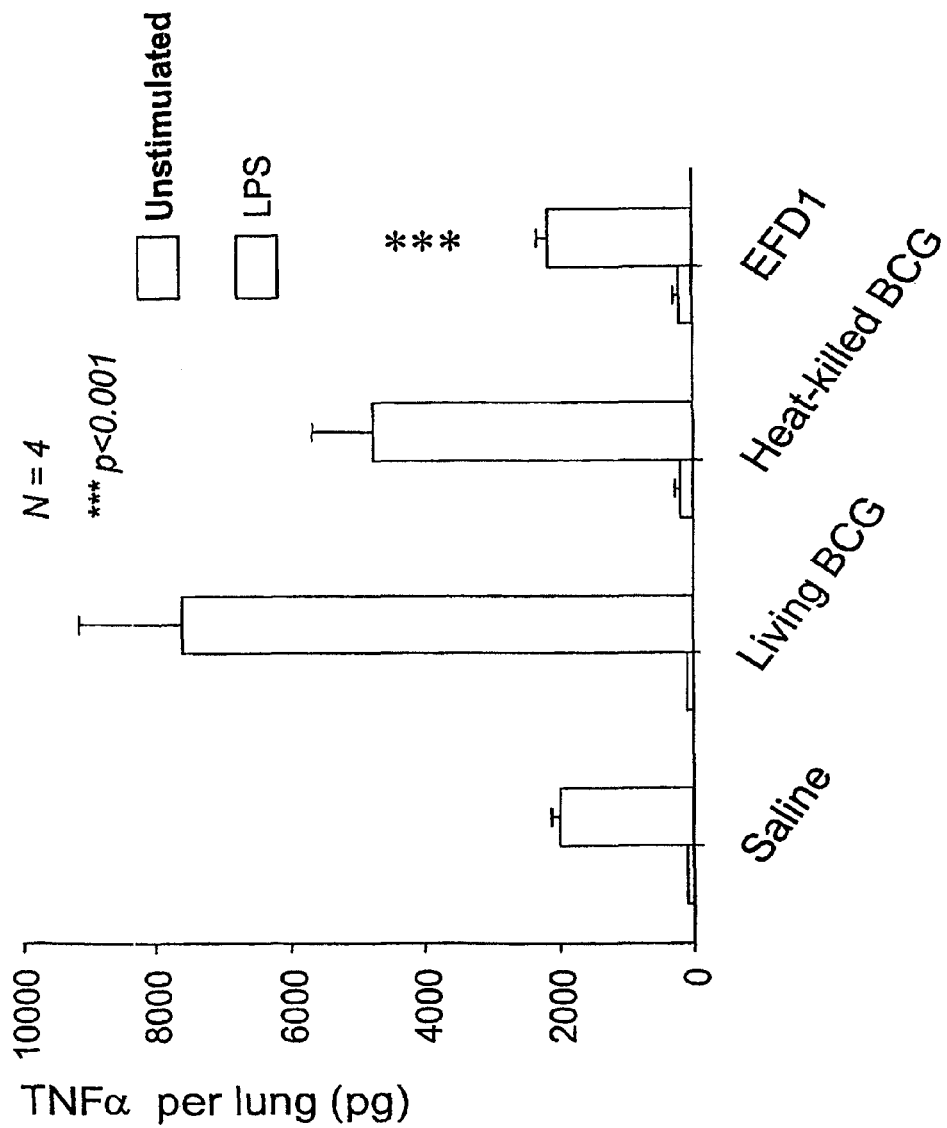

FIG. 24 illustrates the reduced TNF-α production after LPS stimulation of lung explants 18 days after intravenous injection of extended freeze-dried killed. BCG (EFD1), by comparison with injection of living BCG and heat-killed BCG by the same route. No significant production of TNF-α (***p<0.001) in the extended freeze-dried killed BCG group compared to the untreated group. By comparison significant production of TNF-α is observed in the living BCG and heat-killed BCG treated groups.

Figure 25:
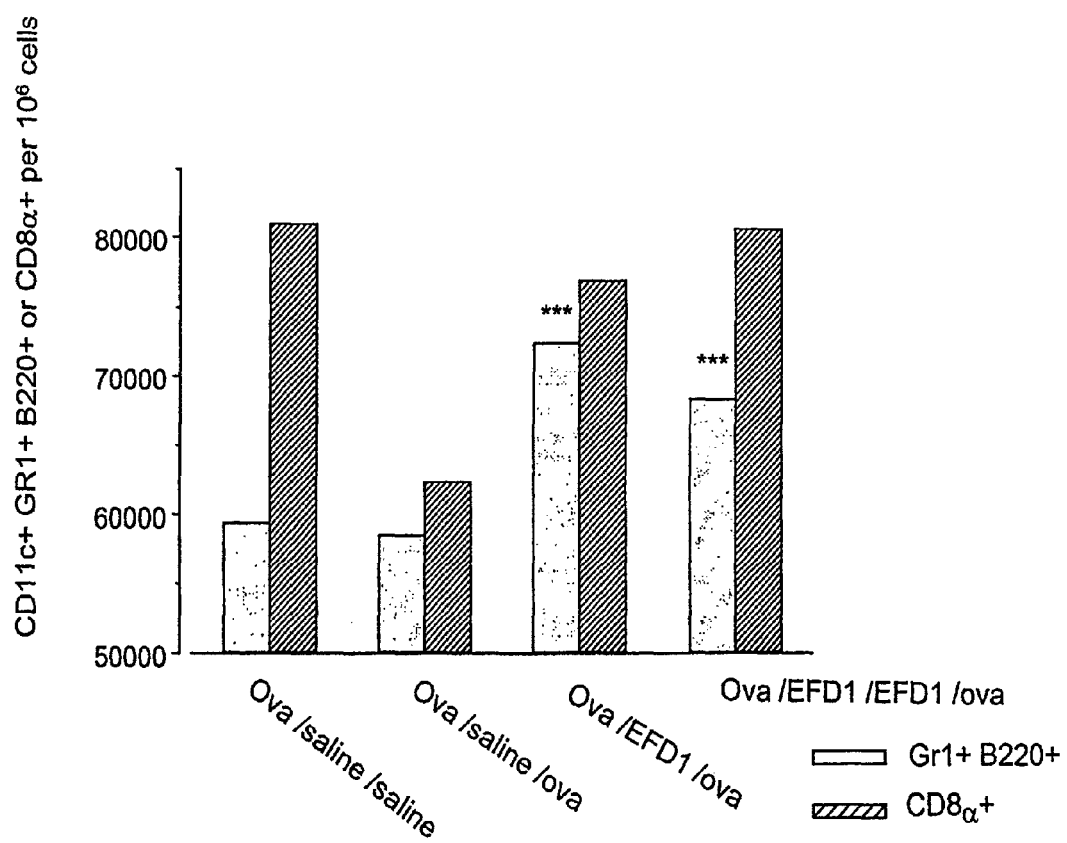

FIG. 25 illustrates the increase of the $CD11c^+$ $Gr1^+$ $B220^+$ plasmacytoid dendritic cells number in the spleen from BALB/c mice immunized 90 days previously with ovalbumin, treated or not with extended freeze-dried killed BCG (EFD1) at days 45 and 65 and challenged or not with ovalbumin. ***Statistically significant increase of the $CD1$ $Gr1^+$ $B220^+$ cells number (p<0.001) in the treated group, no increase of the $CD11c^+CD8α^+$ cells number in the treated group.

Figure 26:
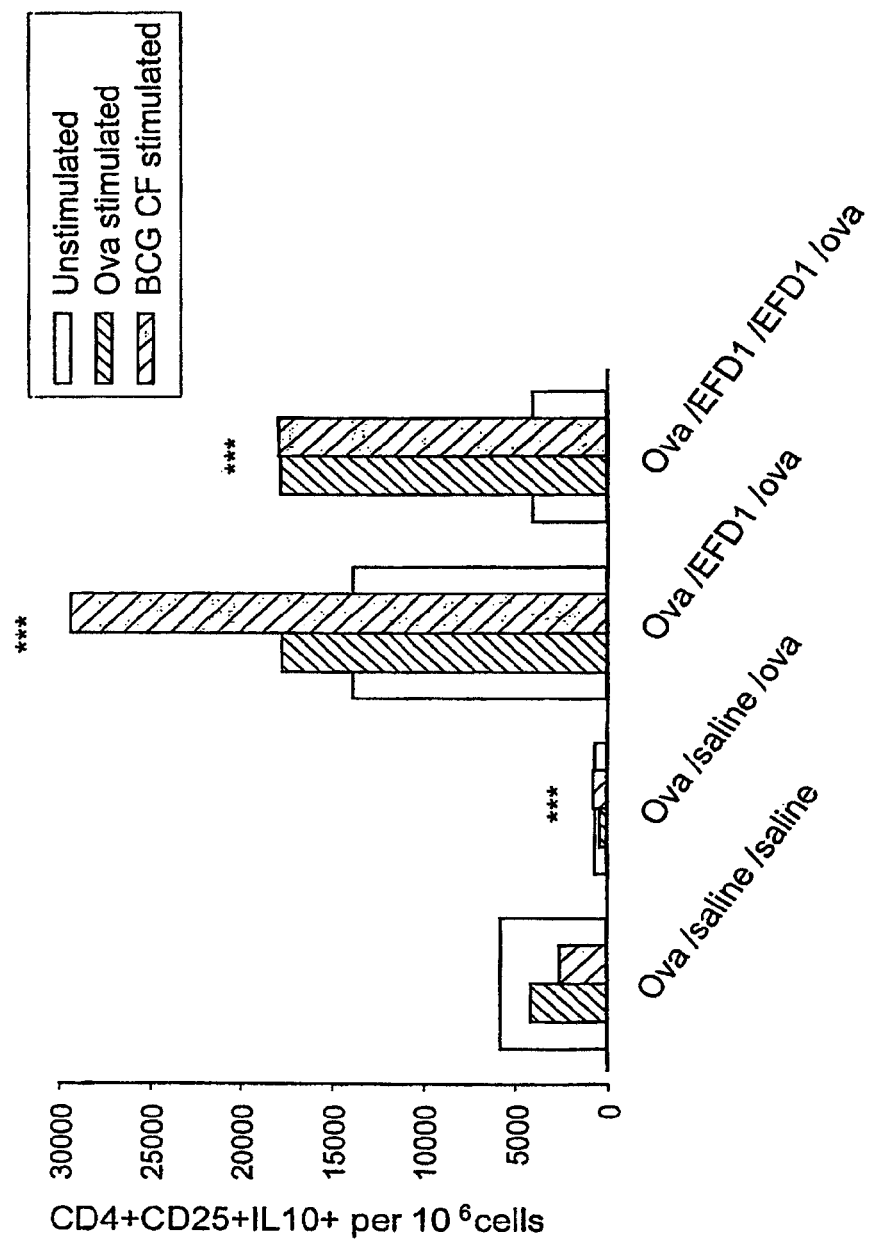

FIG. 26 illustrates the increase of the $CD4^+$ $CD25^+$ $IL-10^+$ cells number in the spleen from BALB/c mice immunized 90 days previously with ovalbumine, treated or not with extended freeze-dried killed BCG (EFD1) at clays 45 and 65 and challenged or not with ovalbumin; spleen cells were stimulated in vitro with OVA or BCG culture supernatant or non-stimulated before analysis of the leukocyte populations. ***Statistically significant increase of the CD4+ CD25+ IL-10+ cells number (p<0.001) in the treated groups.

Figure 27:
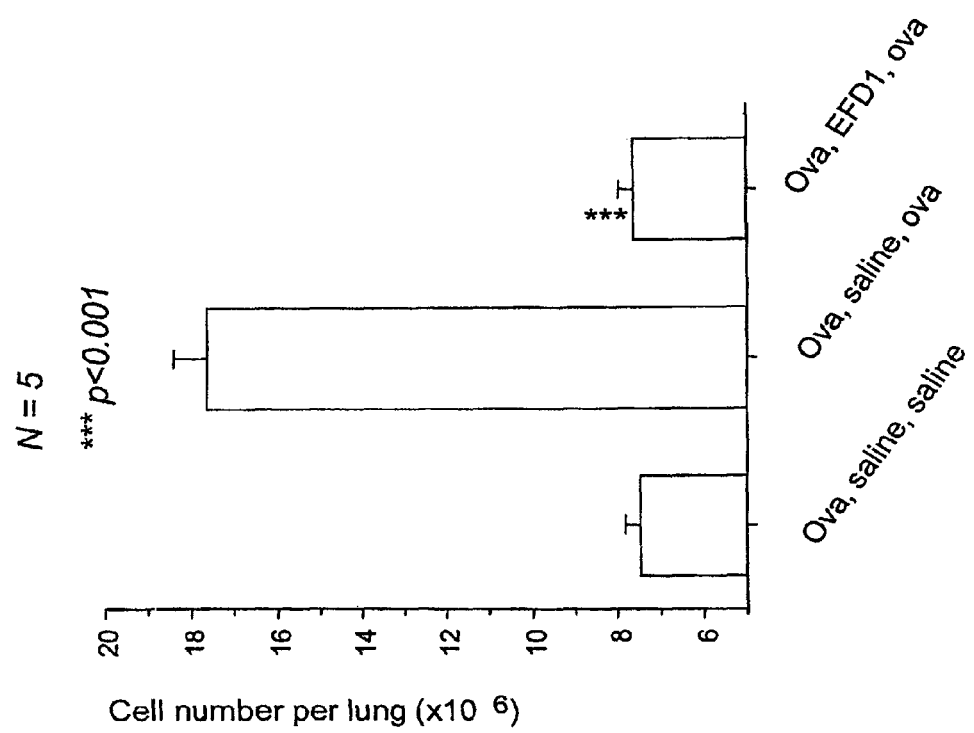

FIG. 27 illustrates the protective effect of extended freeze-dried killed BCG (EFD1) given by the oral route, in the mouse model of asthma, as assessed by lungs cell infiltrate numeration. ***Statistically significant decrease of the lungs cell number in the treated group (p<0.001).

Figure 28:
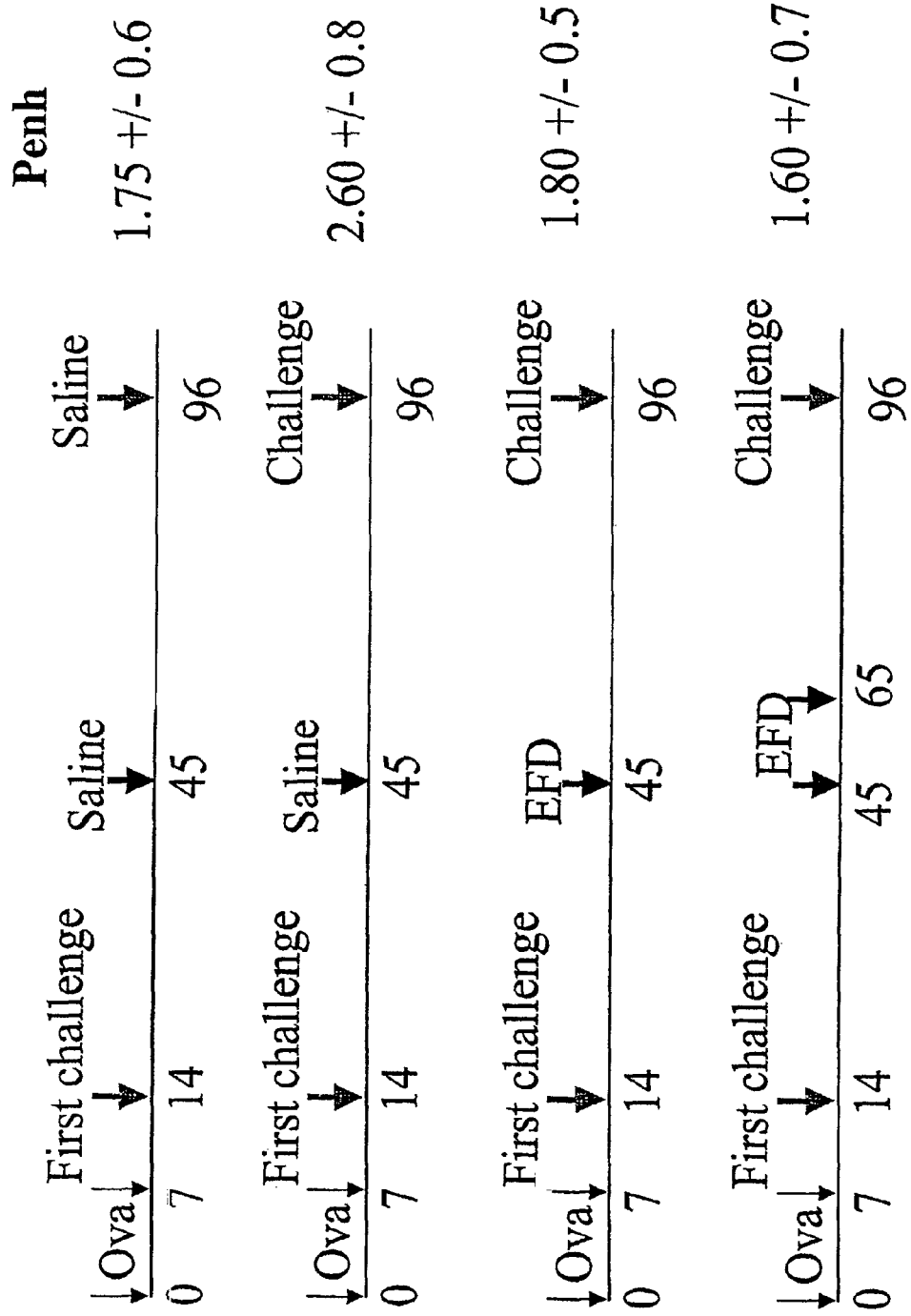

FIG. 28 illustrates the protective effect of one dose of extended freeze-dried killed BCG (EFD) injected by the subcutaneous route, as assessed by the prevention of bronchopulmonary hyper-reactivity in the BALB/c model of asthma.

Figure 29:
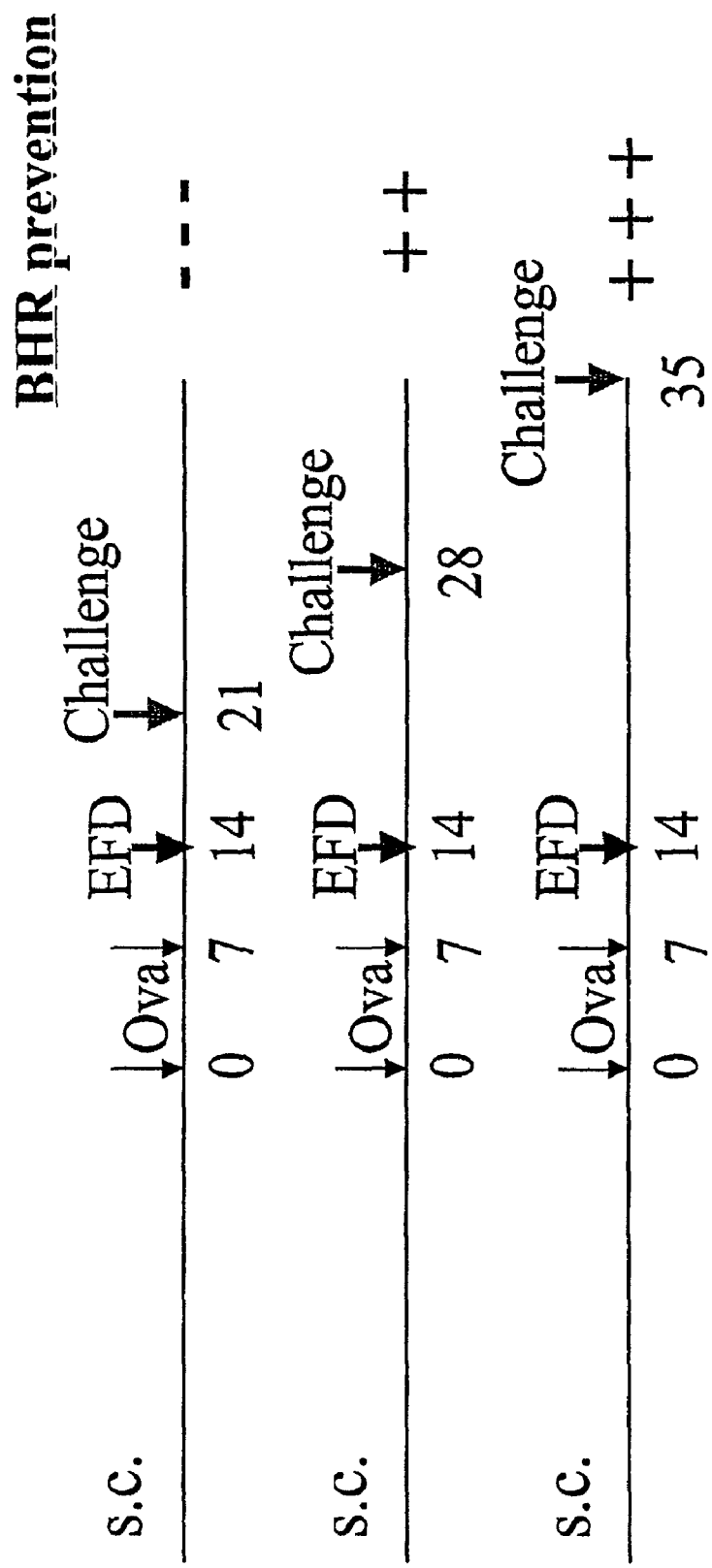

FIG. 29 illustrates the delay of action of extended freeze-dried killed BCG (EFD) injected by the subcutaneous route, as assessed by the prevention of bronchopulmonary hyper-reactivity in the BP2 model of asthma. The prevention of bronchopulmonary hyper-reactivity occurs only if a delay of two to three weeks is present between extended freeze-dried killed BCG administration and challenge.

Figure 30:
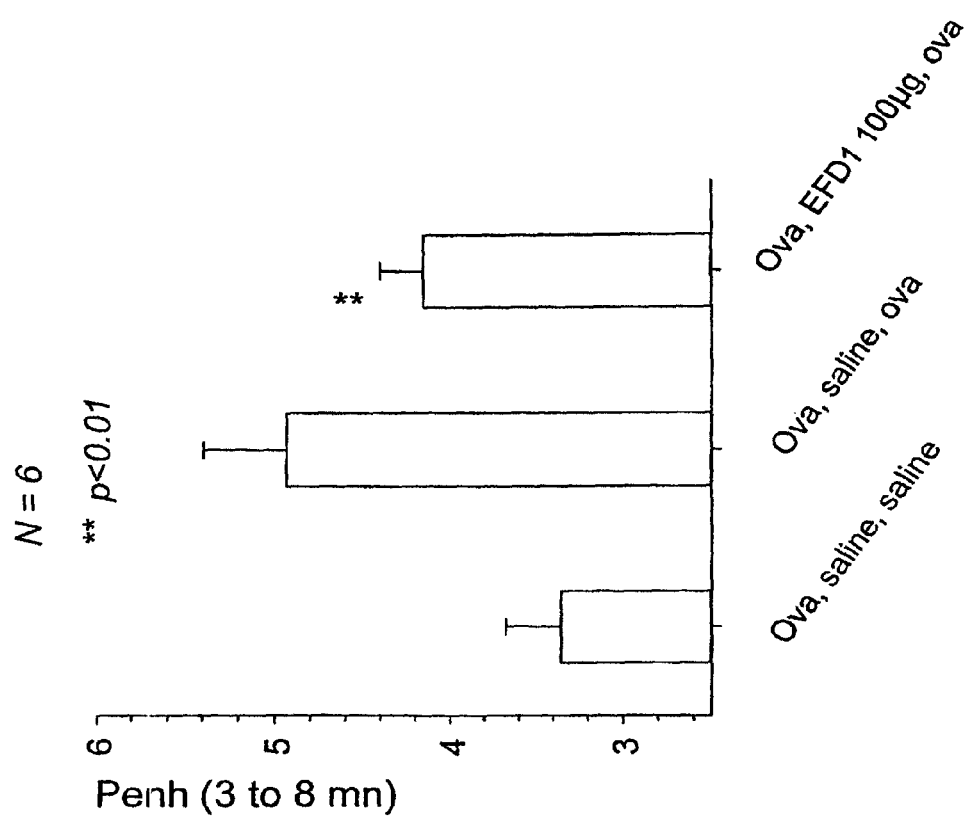

FIG. 30 illustrates the duration of action of extended freeze-dried killed BOG (EFD1), injected by the subcutaneous route, as assessed by the prevention of bronchopulmonary hyper-reactivity in the BP2 model of asthma; the extended freeze-dried killed BCG protective effect persists at least for two months.

EXAMPLE 1

Preparation of Extended Freeze-Dried Killed Mycobacteria

1) Material and methods

The *Mycobacterium bovis* BCG cells (BCG Pasteur vaccine strain 1173P2, deposited at the Collection Nationale de Cultures de Microorganismes, 25 rue du Docteur Roux, 75724 PARIS Cedex 15 (France), on Apr. 24, 1978, under no 1-059 (M. Gheorghiu and coll., 1983, Bull. Inst. Pasteur, 81, 281-288) are grown in sterile Sauton medium (HOOCCH(NH$_2$O)CH$_2$CONH$_2$H$_2$O (asparagine), 4 g/l; C$_6$H$_8$O$_7$; H$_2$O (citric acid), 2 µl; K$_2$HPO$_4$ (di-potassium hydrogenophosphate), 0.5 g/l; MgSO$_4$—H$_2$O (magnesium sulphate), 0.50 g/l; FeIII citrate, 0.05 g/l; glycerol, 60 ml; Zinc sulphate solution (0.155 g Zinc sulphate in 10 ml pyrogen free water), 240 µl/l, pH 7). More precisely the 1173 P2 strain is grown in 250 ml spherical culture flask containing 130 ml sterile Sauton medium, at 37° C., for 14 days, corresponding to the time the culture ends its exponential phase.

The culture is then centrifuged at 2000 g for 10 minutes, at 4° C. to pellet the BCG cells. The cell culture supernatant is discarded and the pellet is washed extensively (three times) in distilled water; each wash consists in resuspending said pellet in distilled water (20 volumes of water per volume of cell-pellet) and centrifuging the cells at 2000 g for 10 minutes, at 4° C.

After the last wash, the pellet is resuspended in a volume of distilled water equivalent or twice that of the volume of the pellet. 20 g of bacteria in 50 ml of water is layered and frozen on the wall of bottles, in order to form a layer of approximately 1 cm in thickness. The mixture is freezed at −60° C.

Figure 1:
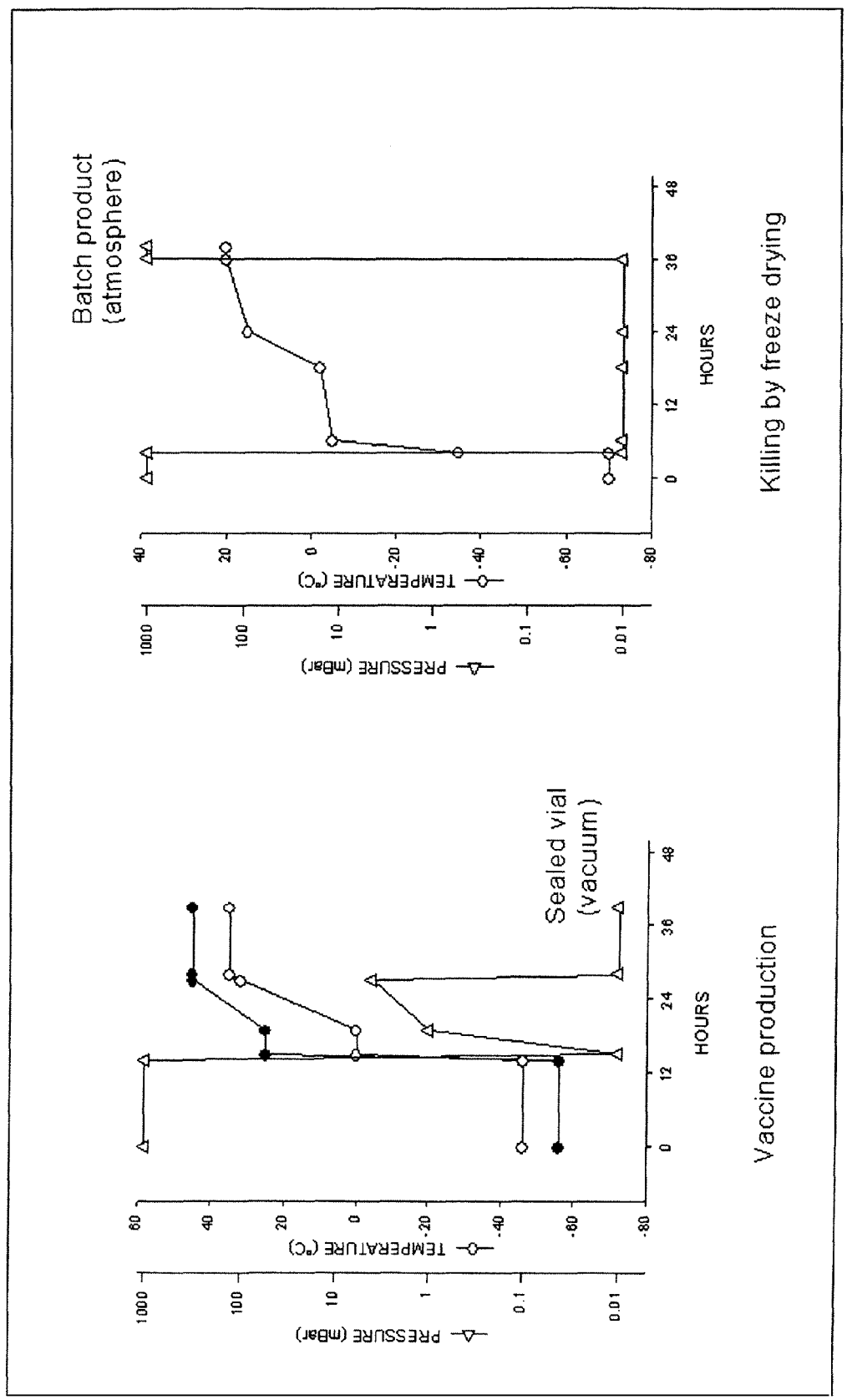

The frozen suspension of cells in water is then extended freeze-dried under the conditions of the extended freeze-drying protocol described in FIG. 1B, to remove essentially all the water (residual water<1.5%). Briefly, the pressure is rapidly decreased to 0.150 mBar, the temperature of the ice condenser being approximately—−50° C. to −54° C., and the freeze-drying process begins. The samples remain frozen, the temperature being not exactly monitored. The pressure is then maintained at 0.1 mBar for 34 h, in order to remove essentially all the water (residual water<1.5%). There is a progressive increase up to room temperature (approximately 20° C.). At the end of the drying, the pressure is then slowly returned to atmospheric pressure with air, at room temperature (approximately 20° C.) and the extended freeze-dried killed BCG cells (approximately 2 g) are harvested and stored at room temperature, under air atmospheric pressure.

The residual water present in the extended freeze-dried killed BCG preparation is determined using the coulometric method from Karl Fisher and a 756 KF Coulometer (METHROM), according to the manufacturer's instructions.

The presence of viable cells in the extended freeze-dried killed preparation is verified by:
  determination of the number of colony forming units (CPU) per ml; 0.2 ml of a suspension of the extended freeze-dried killed preparation (1 mg, e.g. approximately 10$^9$ extended freeze-dried killed BCG cells in water) are plated on Middlebrook 7H10 agar medium (DIFCO), and the plates are incubated at 37° C. for one month, and/or
  staining with the fluorescent dye CFDA-SE (Carboxyfluorescein diacetate-Succimidyl Ester; MOLECULAR PROBES reference number C-1157) which stains viable cells only 1 ml of a suspension of the extended freeze-dried killed preparation (approximately 10$^8$ extended freeze-dried killed BCG cells in water) are mixed with 100 µl of a 1/100 dilution in PBS of CFDA reagent (stock solution: 1 mg/ml in DMSO). The mixture is incubated in the dark at room temperature for 60 min. Labeled bacteria are centrifuged at 3000 rpm for 15 minutes, washed twice in PBS and resuspended in the same buffer. Then, the presence of viable cells was examined by fluorescence microscopy.

2) Results

BCG cells were extended freeze-dried killed following the extended freeze-drying protocol described in material and methods and summarized in FIG. 1B. By comparison, BCG cells were freeze-dried following the standard method for preparation of live BCG vaccine: BCG cells (strain 1173P2) were cultured in Sauton medium at 37° C., harvested at the end of the exponential phase by centrifugation and the BCG cell pellet was resuspended in sodium glutamate (1.5 g/100 ml H$_2$O), at the concentration of 4 mg/ml of BCG). The BCG suspension was distributed in vials (0.25 ml/vial), freeze-dried according to the protocol illustrated in FIG. 1A and each vial containing 1.5±0.5% H$_2$O was stored at room temperature under vacuum (0.06 mBar).

The vialibility of the BCG cells in the different preparations was assayed as described in Material and Methods.

The following results were observed by the coulometric method of Karl Fisher, the culture assay and by the CFDA-SE staining test:
  200 mg of extended freeze-dried killed BCG preparation contained 1.073 mg if water in a representative determination, which is equivalent to less than 0.5% residual water.
  no living bacteria were detected in the extended freeze-dried killed BCG samples prepared according to the method of the invention,
  50% to 60% living bacteria were detected in the freeze-dried killed BCG preparation according to the standard BCG vaccine preparation method.

EXAMPLE 2

Preparation of Extended Freeze-Dried Killed Mycobacteria Fractions

1) Delipidated Fraction (Fraction A)

10 mg/ml of approximately $10^{10}$ extended freeze-dried killed BCG cells, suspended in borate buffer ($Na_2B_4O_7$ $10H_2O$ 0.363%; $H_3BO_3$ 0.525%; NaCl 0.619% and Tween 20 0.0005% in distilled water, pH 8), were centrifuged at 12 000 g for 10 minutes and the supernatant was discarded. The pellet was resuspended in 1 ml of chloroform/methanol (9/1) for 24 b at room temperature to extract lipids. The chloroform/methanol is removed by centrifugation at 12 000 g per 10 min. The delipidated pellet from the chloroform/methanol extraction was vacuum-dried.

2) Deglycosylated Fraction (Fraction B)

10 mg/ml of approximately $10^{10}$ freeze-dried killed BCG cells, suspended in borate buffer ($Na_2B_4O_7$ $10 H_2O$ 0.363%; $H_3BO_3$ 0.525%; NaCl 0.619% and TWEEN 20 0.0005% in distilled water, pH 8), were centrifuged at 12 000 g for 10 minutes and the supernatant was discarded. The pellet was resuspended in 1 ml of 0.1 Sodium acetate, for 24 h at 37° C., containing 1 mg lysozyme to remove the peptidoglycan. The digestion product was heated 2 min at 96° C. and the pellet was harvested by centrifugation for 1 h at 12 000 g.

3) DNase and RNase Treated Fraction (Fraction C)

10 mg/ml of approximately $10^{10}$ extended freeze-dried killed BCG cells, suspended in borate buffer, were centrifuged at 12 000 g for 10 minutes and the supernatant was discarded. The pellet was resuspended in 1 ml of 40 mM Tris-HCl buffer containing 1 mg DNase and 1 mg RNase and 5 mM $MgCl_2$, for 24 h at 37° C., to remove the nucleic acids. The digestion product was heated 2 min at 96° C. and the pellet was harvested by centrifugation for 1 h at 12 000 g.

4) Protease Treated Fraction (Fraction D)

10 mg/ml of approximately $10^{10}$ extended freeze-dried killed BCG cells, suspended in borate buffer, were centrifuged at 12 000 g for 10 minutes and the supernatant was discarded. The pellet was resuspended in 1 ml of 0.1 M ammonium acetate buffer containing 0.1 mg subtilisin, for 23 h at 37° C. To remove the protein completely, 0.1 mg subtilisin was then added to the reaction mixture and incubated for 7 h at 37° C. The digestion product was heated 2 min at 96° C. and the pellet was harvested by centrifugation for 1 h at 12 000 g.

5) Successive Treatments (Fraction E)

10 mg/ml of approximately $10^{10}$ extended freeze-dried killed BCG cells were centrifuged at 12 000 g for 10 minutes and the supernatant was discarded. The pellet was resuspended in borate buffer and treated successively with chloroform/methanol (9/1), lysozyme, DNAse-RNase mixture and subtilisin as described above. The digestion product was heated 2 min at 96° C. and the pellet was harvested by centrifugation for 1 h at 12 000 g.

6) Characterization of the Protein and Polysaccharide Content of the Extended Freeze-Dried Killed BCG Preparation.

a) Material and Methods

A preparation of extended freeze-dried killed BCG preparation (10 mg) was suspended in 1 ml of 4% butanol in water and distributed in two eppendorf tubes (500 µl per tube) containing 1 g of zirconia/silica beads (0.1 mm) (BIOSPEC PRODUCTS, INC.). The tubes were then placed in a Mixer Mills (MM301, RESCH) at a frequency of 25 during 5, 15, 30, 60, 120, 180, 240, 300 or 470 minutes. The tubes were then centrifuged at 10000 rpm for 30 min; the supernatant was recovered, filtered (0.22 µm filter, MILLIPORE) and the protein, the amino acids and the polysaccharide concentrations were determined as follows:

total protein concentration was determined using Micro BCA Protein Reagent Kit (PIERCE), amino-acids concentration determination and analysis was determined by mass spectrometry total polysaccharide concentration was determined using anthrone method, according to S. Melvin, *Anal. Biochem.* 1953, 25, 1656-.

Aliquots (5 µg of proteins) of the bacteria extracts collected at 5, 60 or 300 min were separated by SDS-PAGE, the protein were then transfererred onto a PVDF membrane and either stained with Aurodye® (Pharmacia) or with polyclonal antibodies directed to mycobacterial proteins.

b) Results

The bacteria extracts collected after 5, 60 or 300 min of extraction contains respectively 280, 500 and 1258 µg of proteins; 190, 420 and 880 µg of amino acids and 697, 1267 and 1765 µg of polysaccharides.

The results presented in FIG. 16 show that the extended freeze-drying process preserves the structure of the proteins which are present in the killed BCG preparations as indicated by the presence of discrete protein bands without smear; the protein profile observed with the extended freeze-dried killed BCG preparation extracts is comparable to that obtained with living BCG preparations.

EXAMPLE 3

Protective Effect of Extended Freeze-Dried Killed Mycobacteria on Asthma in a Mouse Model 1) Material and Methods a) Animals Male adult (6 to 7 weeks old) BP2 ($H-2^q$) mice were obtained from the Centre d'élevage R. Janvier (Le Genest, Saint Isle, France) and were maintained in animal facilities in specific pathogen free-conditions.

b) Mouse Model of the Asthma-Like Allergen Specific Disease

Male adult BP2 mice were immunized by the subcutaneous route (in the dorsal part of the neck) with 1 µg ovalbumin (OVA; ICN Laboratories) and 1.6 mg aluminium hydroxide adjuvant in saline (0.4 ml final volume), on days 0 ($D_0$) and 7 ($D_7$). The allergic response is provoked by intranasal challenge with 10 µg OVA in 50 µl saline on day 96-98. Alternatively, a water soluble ray-grass pollen extract is used as an allergen, in the same conditions as for OVA except that 10 µg is used for immunization.

c) Preparation of the Mycobacterial Immunomodulatory Composition

Extended freeze-dried killed BCG, prepared as described in example 1 were tested as an asthma vaccine in the BP2 mouse, by comparison with the following BCG preparations:

Living BCG

The *Mycobacterium bovis* BCG Pasteur vaccine strain 1173P2 was grown as dispersed bacilli in Beck-Proskauer medium (Gheorghiu and coll., 1988, *J. Biol. Standard.*, 16, 15-26)) supplemented with 0.05% Triton WR 1339 (SIGMA) and 6% glucose. The bacteria were harvested at the exponential phase (5 to 7 days) and stored at −70° C. in Beck-Proskauer medium supplemented with 0.05% Triton and 6% glycerol. The number of colony forming unit (CFU) per ml was determined by plating suitable dilutions in phosphate-buffered saline (PBS) on Middlebrook 7H10 agar medium (DIFCO). The suspension was diluted at the concentration of $10^8$, $10^9$ or $10^{10}$ CFU/ml in PBS just before its injection (100 μl).

Heat-Killed BCG

Living BCG prepared as above described was centrifuged at 3000 rpm for 15 minutes and the supernatant was discarded. The pellet was resuspended in saline, for example in a buffer containing borate ($Na_2B_4O_7$ $10H_2O$ 0.363%; $H_3BO_3$ 0.525%; NaCl 0.619% and Tween 20 0.0005% in distilled water, pH 8), and the suspension was autoclaved for 15 min at 115° C.

d) Curative Protocol of Administration: of Extended Freeze-Dried Killed Mycobacteria in The Mouse Model of Asthma Male adult BP2 mice are immunised with OVA as described above. Groups of 25 mice were injected with 100 μl of the BCG compositions prepared as described above.

living BCG vaccine strain 1173P2 ($10^7$ CFU)
  heat-killed BCG ($10^8$ bacteria corpses which are equivalent to $10^7$CFU
  extended freeze-dried killed BCG (10 μg to 10 mg; 10 μg is equivalent of $10^7$CFU), and
PBS, by the subcutaneous route (base of the tail), on $D_{42-45}$ and $D_{65-70}$ after the first immunisation with OVA.

The allergic response is provoked by intranasal challenge with 100 μg OVA in 50 μl saline on day 96-98; PBS alone is administered intranasally for comparison.

e) Broncho-Pulmonary (BHR) Analysis

A barometric plethysmographic equipment (BUXCO) that allows BHR study on unanesthetised animals was used Animals immunized with OVA, treated with the different BCG preparations or non-treated were tested 24 h after the challenge with OVA or water soluble ray-grass pollen extract. The animals were placed in a plethysmographic chamber. Their basal ventilation parameters were recorded and during 20 s or 1 minute they received inhalation of methacholin (ALDRICH), 100 mM in $H_2O$ by using standard nebuliser, and their ventilation parameters were recorded during 10 minutes after methacholin aerosol administration. Reduction of the ventilation during the period is reported (area under the curve) and the bronchopulmonary resistance was expressed as enhanced pause (Penh), calculated as: (expiratory time(tE)/40% of relaxation time (tre1)–1)× peak expiratory flow (PEF)/peak inspiratory flow (PIP)×0.67, according to the manufacture' instructions. Every minute an average value of Penh was recorded. For the graphic representation, each value was expressed for every minute.

f) Bronchoalveolar Lavage (BAL)

Mice were anesthetised by the intraperitoneal route with a lethal dose of urethane (1.5 g/kg; SIGMA). Circulating blood was removed from the abdominal aorte and a canula connected to a syringe was placed in the trachea, and the lungs were washed three times with 0.7 ml PBS and the lavage was collected in a tube and kept on ice.

The number of cells present in the BAL was determined in an automatic counting equipment (MI), provided by COULTER. To determine the percentages of the different cell types (eosinophils, neutrophils, macrophages), the BAL cells which have been cytospinnned on glass slides, were stained with DIFF QUICK (BAXTER).

g) Fibronectin Assay

BAL were centrifuged at 1000 rpm for 10 min at 4° C. and the fibronectin present in the supernatant was assayed by competition Enzyme Immunometric Assay (EIA), following standard protocols (Renard and coll., Anal. Biochem., 1980, 205-214).

h) Preparation and Analysis of Pulmonary Explants

The lungs were cut in small pieces of approximately 1 mm per 3 mm. Four or five pieces from each lung were placed in a well of a tissue culture plate containing 1 ml of AIM V culture medium (Life Technologies). The pulmonary explants were cultured in medium alone for basal level determination; alternatively BCG culture filtrate (10 μg/ml) was added to the culture to reveal mycobacterial specific cells, or anti-CD3 monoclonal antibody was added to the culture to reveal reactivity of T lymphocytes. 24 h later, the presence of different lymphokines (IFN-γ, TNF-α, IL-10 . . . ) was assayed by ELISA using commercial kits, according to the manufacturer's instructions.

The entire lung (without trachea) was dissociated in collagenase and DNase medium to enumerate the infiltrating cells on a Flow cytometer using various monoclonal antibodies labelled with different fluorochromes.

i) Histopathological Analysis of the Lungs

The entire lungs were fixed in buffered formaldehyde and processed for histopathological analysis. The Schiff staining was used to stain the mucus and the mucus containing cells. The hematoxy-eosin stain was used as a counter staining. The slides were examined and an evaluation of cell infiltration and mucus content was performed by one observer who scored the slide without knowledge of the origin of the sample (blind assay).

j) Cytokines Assay

The cytokines which are either present in the serum and the BAL samples from the groups of immunised mice, or secreted by the lung explants cultures from these mice, were assayed as follows: IFN-γ, IL-10 and IL-12 were tested by ELISA; TNF-α and IL-5 were tested by EIA (Enzyme Immunometric Assay).

k) OVA-Specific IgE Assay

The level of OVA-specific IgE present in the serum was assayed by ELISA, following standard protocols (Hansen and coll., J. Immunol., 2000, 223-230).

l) Statistical Analysis

The number (n) of animals per group was 4<n<8. The student's two-tailed (t) test was performed for independent events.

2) Results a) Broncho-Pulmonary (BHR) Analysis

Animals immunised with OVA or a water soluble ray-grass pollen extract and treated with the different BCG preparations, or non-treated, were tested 24 h after the challenge with OVA or ray-grass pollen.

The model chosen in these studies, using BP2 mice with Th2 background which are immunised with ovalbumine associated with aluminium hydroxide, a more potent adjuvant of allergic reaction than the freund incomplete adjuvant, is thus more stringent than the model of BALB/c mice immunized with ovalbumine in freund incomplete adjuvant used by CC Wand and coll., precited.

Figure 2:
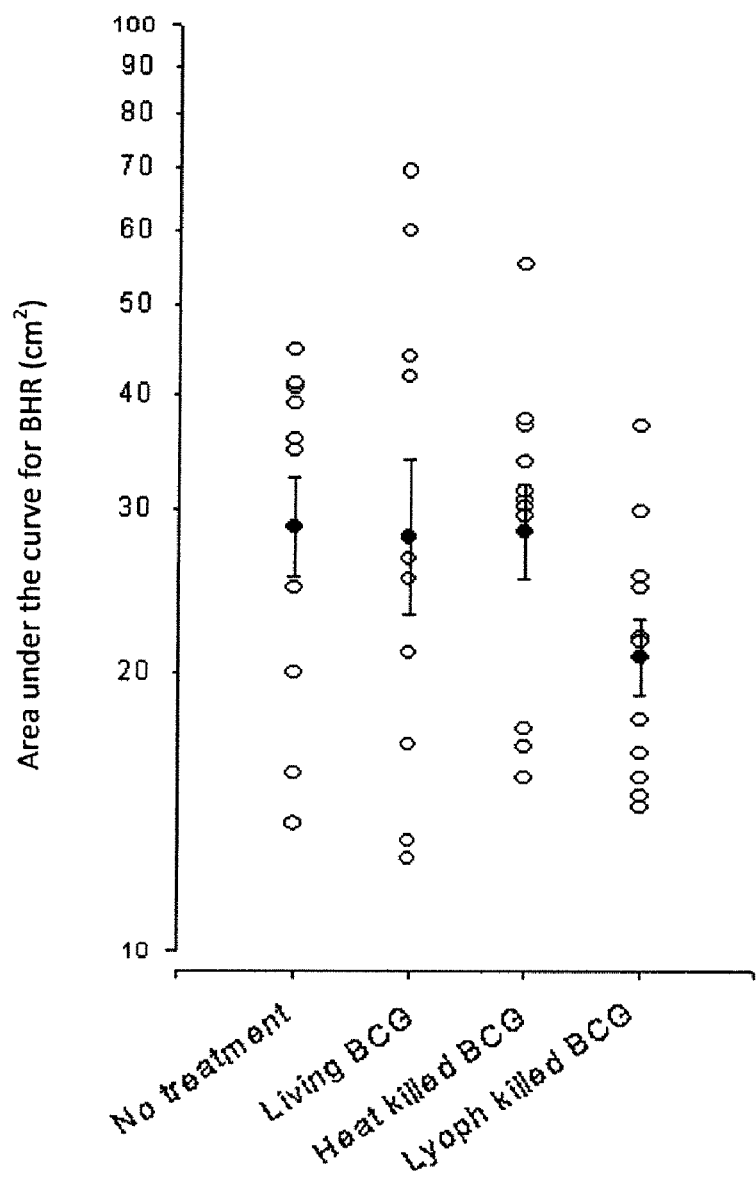
Figure 3:
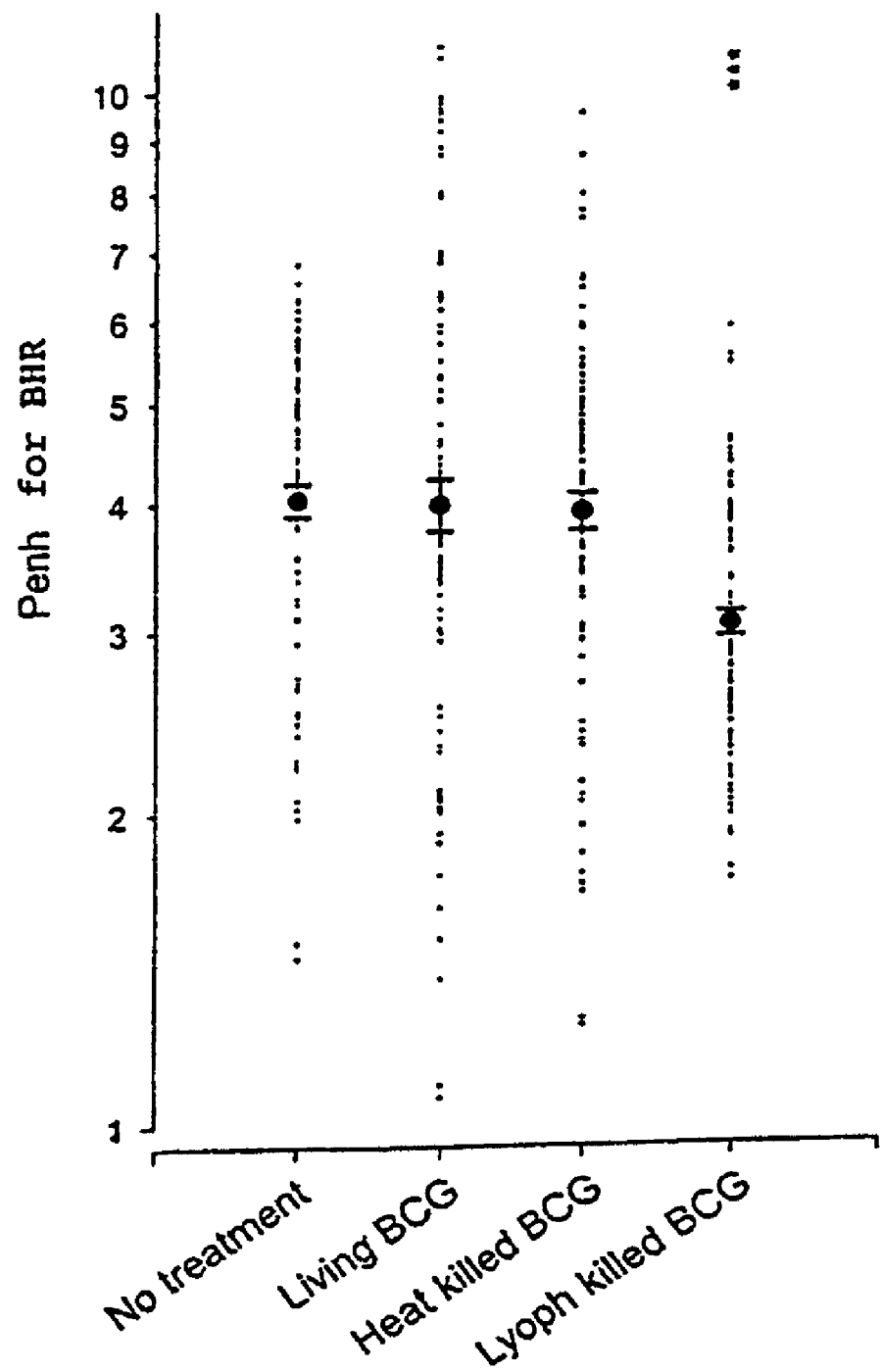
Figure 4:
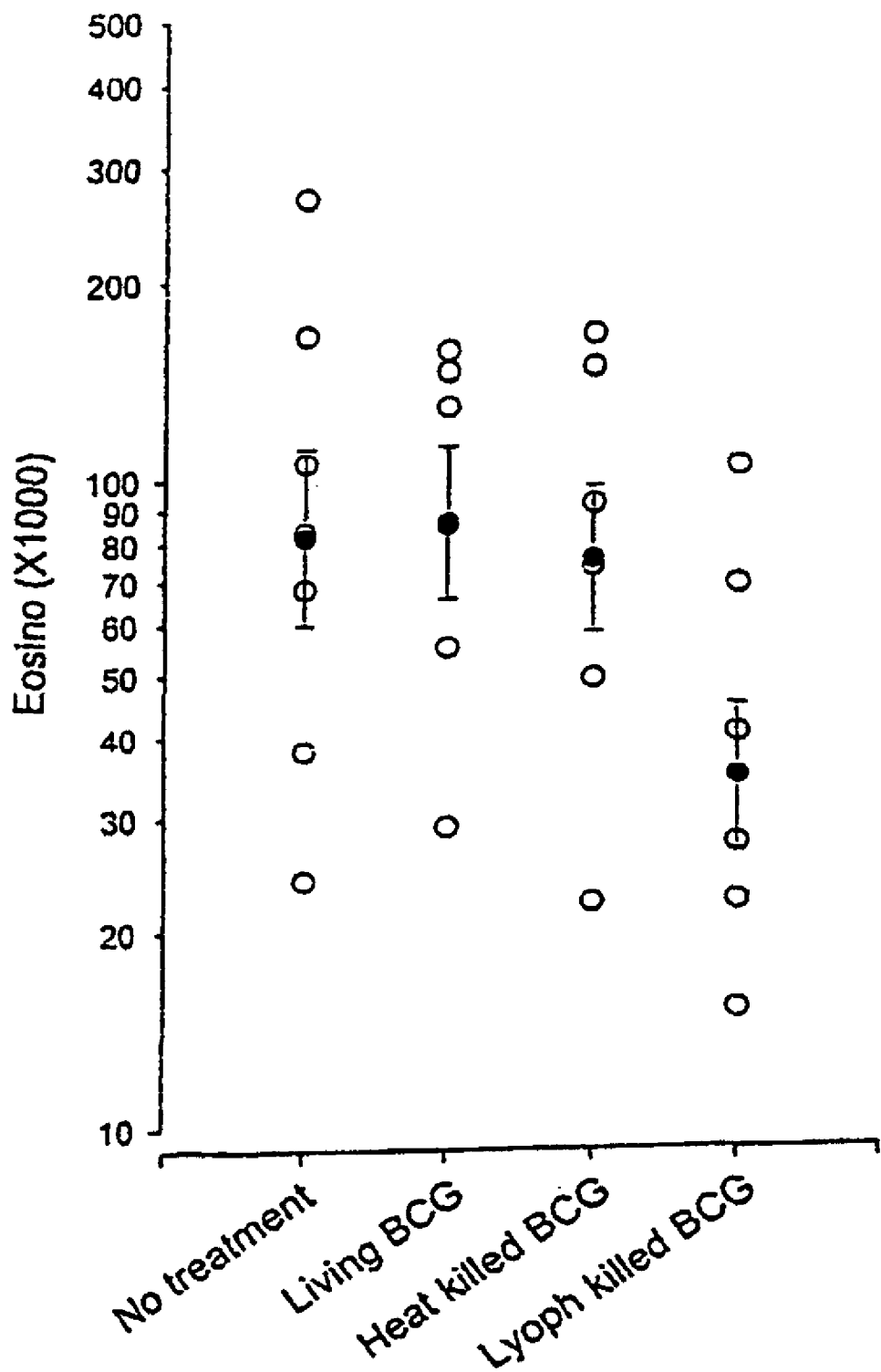
Figure 5:
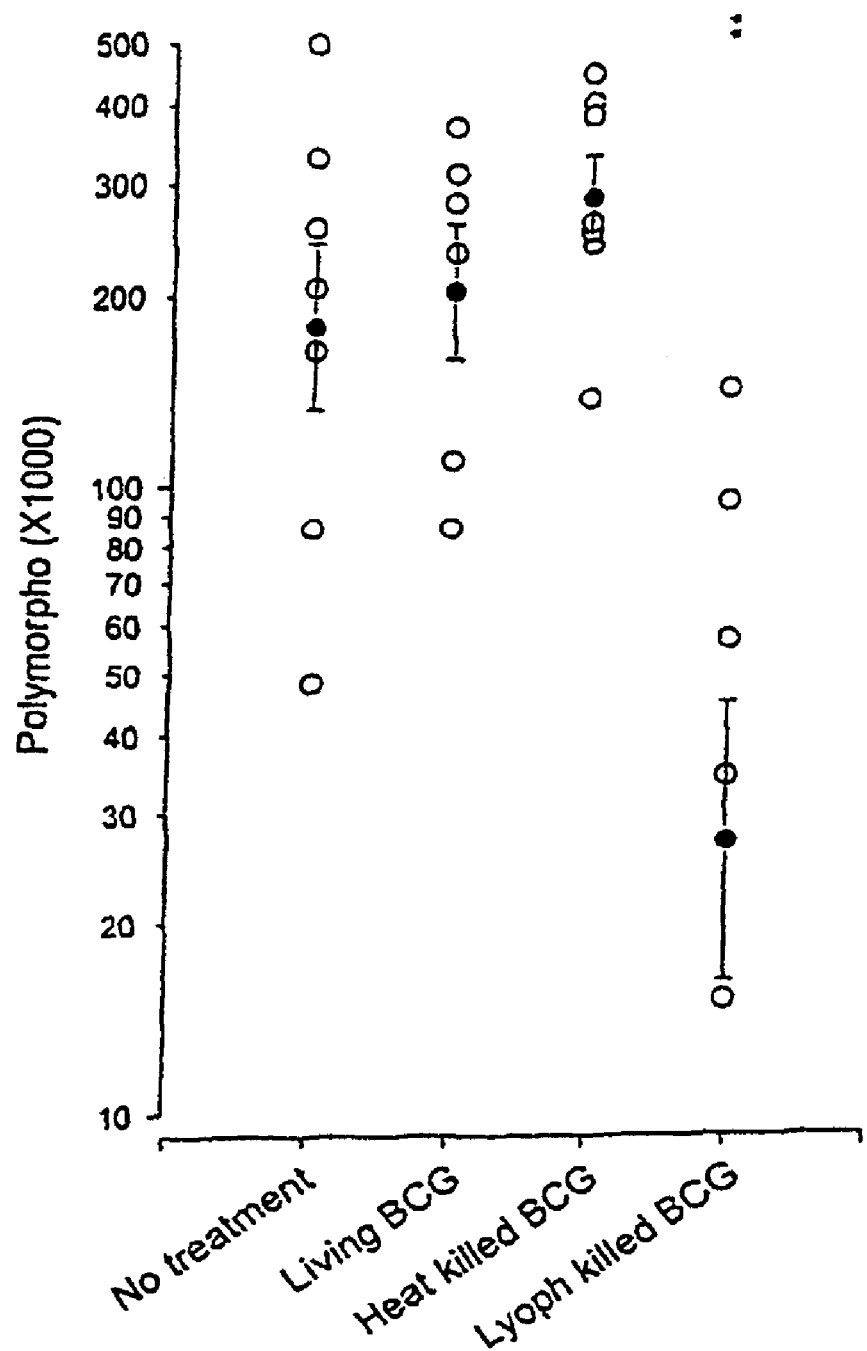

The data presented in FIGS. 2 and 3 indicate that in this stringent model of asthma, extended freeze-dried killed BCG (10 μg) has a statistically significant (p<: 0.001) protective effect on broncho-pulmonary, as expressed by a lower reactivity to metacholine compared to non-treated controls. By contrast, in this stringent model of asthma, no significant protective effect was observed in the animals treated with live BCG ($10^7$ CFU) or heat-killed BCG ($10^8$ bacterial corpses). A similar statistically protective effect (p<0.01) on asthma is observed with the extended freeze-dried killed BCG (EFD) preparation, when a water soluble ray-grass pollen extract is used as an allergen (FIG. 17).

b) Bronchoalveolar Lavage (BAL)

A decrease of the number of eosinophils (p<0.05) and neutrophils (p<0.05) is observed in the groups of mice treated with 10 μg, 100 μg, 1 mg or 10 mg of extended freeze-dried killed BCG (FIGS. 4, 5, 15A, 18A and 18B).

Figure 6:
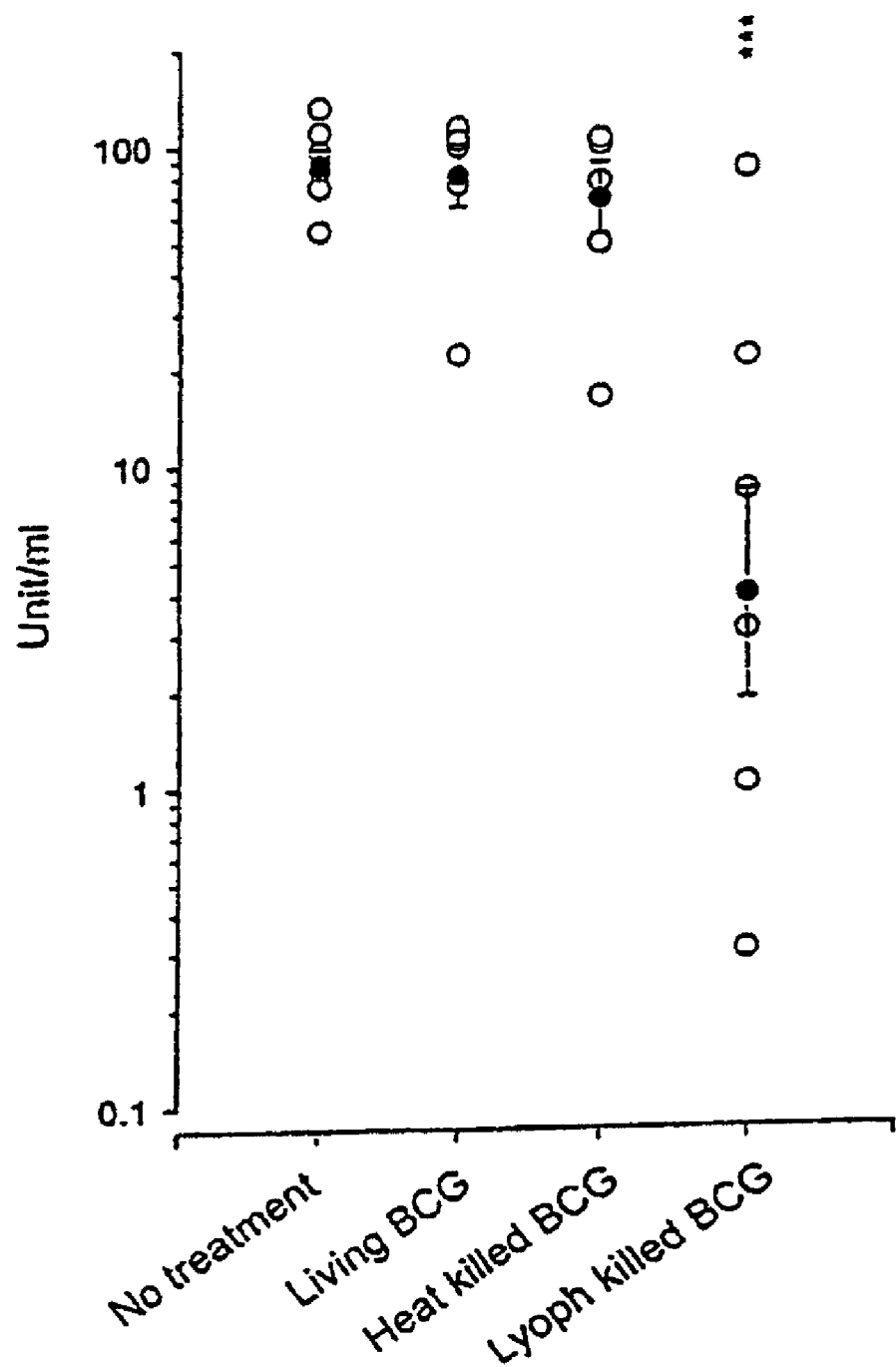

The level of fibronectin present in airways exudation liquid which reflects the inflammatory response, shows a very significant decrease (p<0.001) in the group treated with extended freeze-dried killed BCG (10 μg, FIG. 6).

Figure 7:
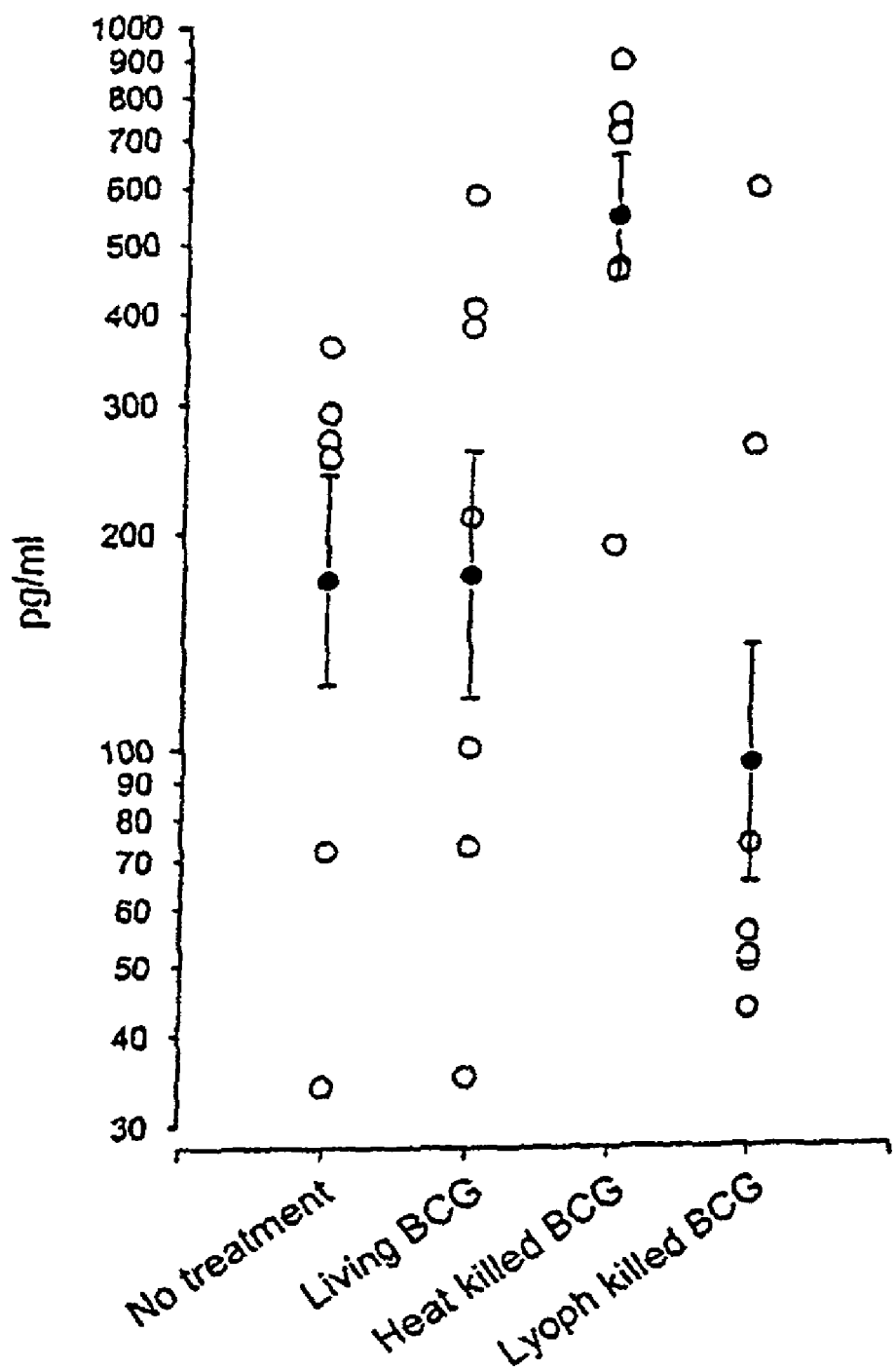
FIG. 7 illustrates the level of IL-5 in bronchoalveolar lavages from groups of mice that have been treated with living BCG, heat-killed BCG, extended freeze-dried killed BCG (Lyoph killed BCG), or non-treated. Data are expressed in µg/ml; individual data (-○-), mean±SEM per group of mice (-●-).
Figure 8:
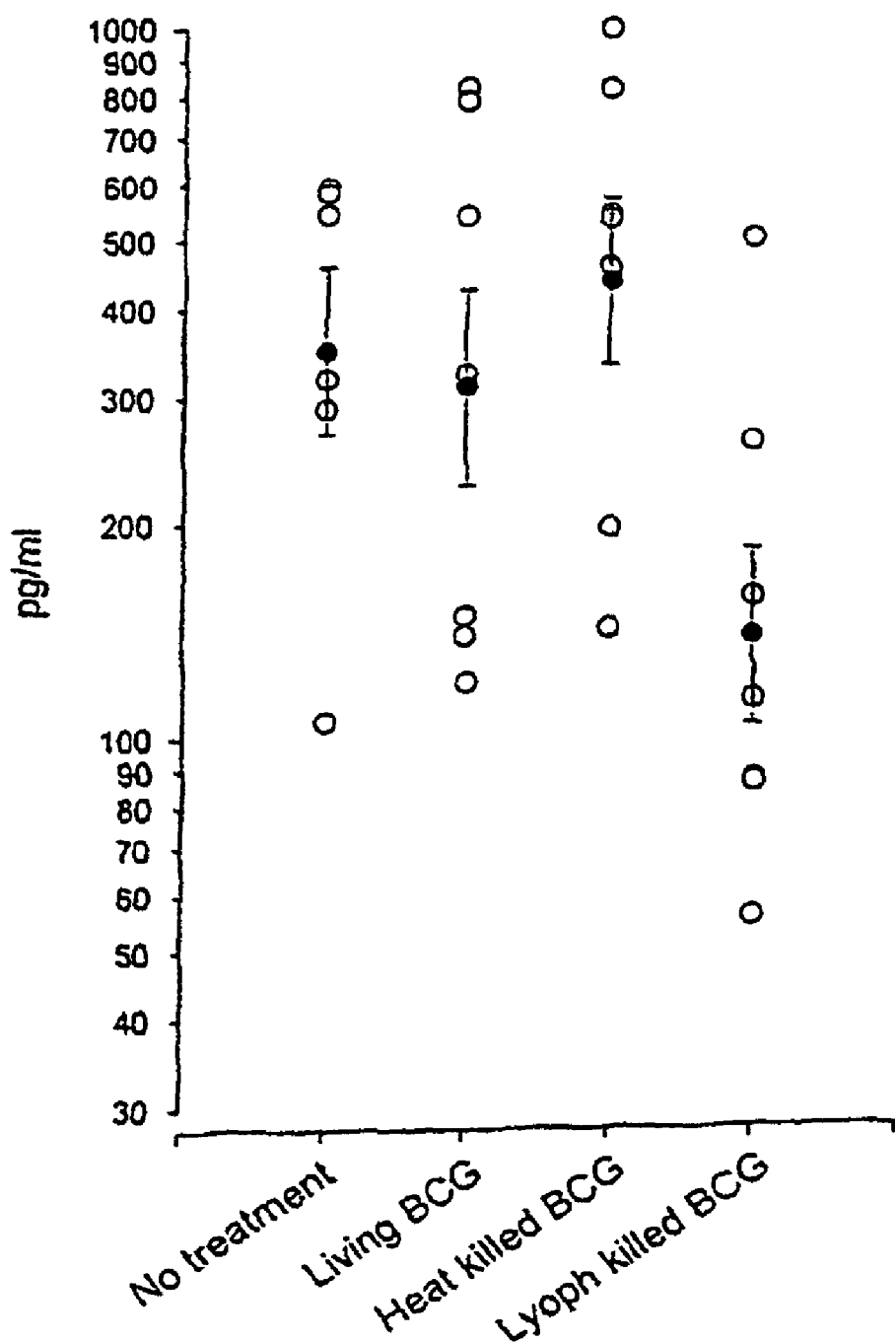
FIG. 8 illustrates the level of IL-5 in the serum from groups of mice that have been treated with living BCG, heat-killed BCG, extended freeze-dried killed BCG (Lyoph killed BCG), or non-treated. Data are expressed in µg/ml; individual data (-○-), mean±SEM per group of mice (-●-).
Figure 15:
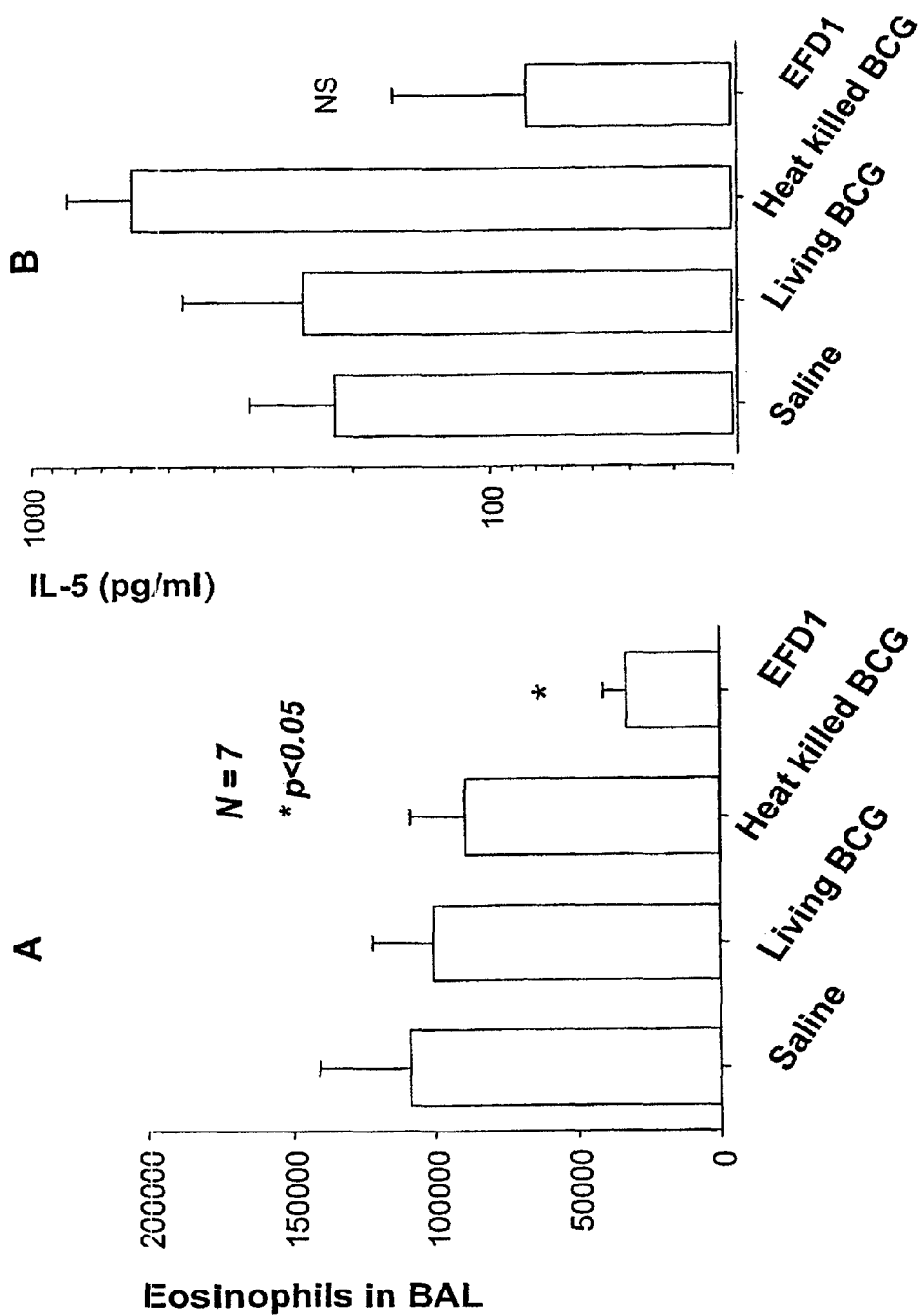

Assays as regards IL-5, a lymphokine implicated in the increase of the number of eosinophils during allergic responses, show a decrease both in BAL and in the blood, in the group treated with extended freeze-dried killed BCG (FIGS. 7, 8 and 15).

Assays as regards IL-4, a Th2 cytokine, shows a statistically significant decrease in BAL from the groups of mice treated with 10 μg, 100 μg, 1 mg or 10 mg of extended freeze-dried killed BCG (FIG. 18C).

By comparison, no significant effect was observed in mice treated with either living BCG ($10^7$ CFU) or heat-killed BCG ($10^8$ bacterial corpses).

These results show that extended freeze-dried killed BCG can induce an immune response capable of treating the symptoms of asthma as demonstrated by the decrease in the inflammatory response of the lung (production of eosinophils and neutrophils, exudation of fibronectin). In this stringent model of asthma (BP2 mace) with Th2 background, no protection was observed in either living BCG or heat-killed BCG treated groups.

c) Analysis of the Histopathology and the Infiltrating Cells of the Lungs

The histopathological analysis of the lungs shows that the treatment with extended freeze-dried killed BCG (EFD) prevents leukocyte infiltration of the lungs and mucosal metaplasia of bronchial epithelia.

These results are confirmed by the flow cytometry analysis of the cells present in the lung tissues which demonstrates that the treatment with extended freeze-dried killed BCG induces a statistically significant (p<0.001) decrease of leukocyte infiltration in the lungs (FIG. 19); analysis of the different leukocyte populations (FIG. 20), shows a decrease of the number of macrophages ($CD11b^+$), polymorphonuclear cells ($Gr1^+$) and dendritic cells ($CD11c^+$) in the lungs of the extended freeze-dried killed BCG treated groups.

d) Cytokine Analysis

Figures 9A, 9B:
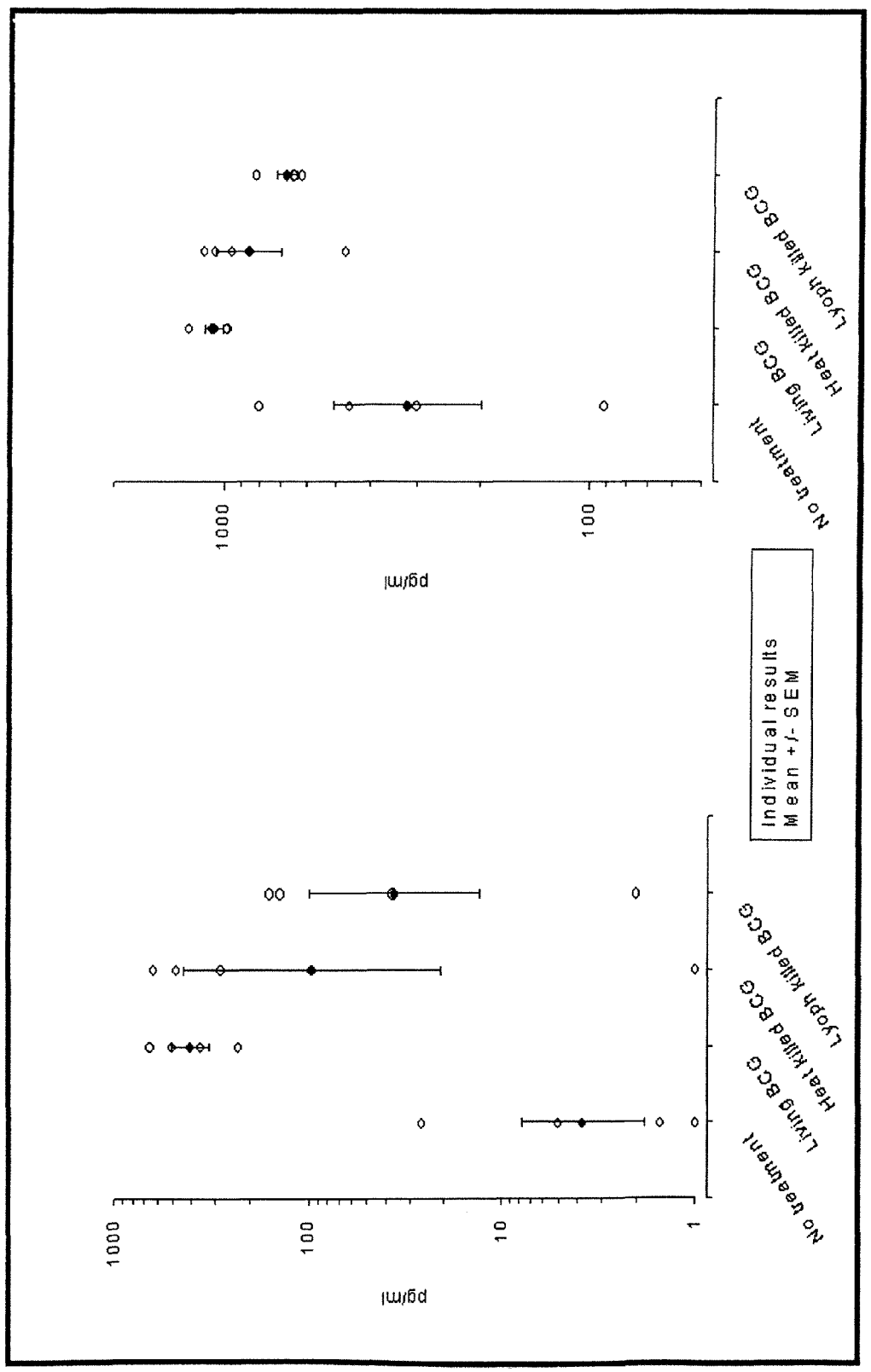
FIG. 9 illustrates the level of IFN-γ (µg/ml) in lung cultures from groups of mice that have been treated with living BCG, heat-killed BCG, extended freeze-dried killed BCG (Lyoph killed BCG), or non-treated; the cultures have been stimulated in vitro with purified BCG secreted protein (A) or with anti-CD3 anti-bodies (B). Individual data (-○-) and mean±SEM per group of mice (-●-) are presented.

Lung biopsies from the groups of mice that have been treated with the different BCG preparations were cultured in the presence or in the absence of non-purified proteins secreted by BCG or anti-CD3 mAb, and the production of IFN-γ and IL-10 was assayed in the supernatant The results presented in FIGS. 9 and 21 indicate that IFN-γ production requires an immunisation with BCG (FIG. 9A). The lower level IFN-γ observed in the extended freeze-dried killed BCG group (FIG. 9A) is not statistically significant from the level observed in the other BCG immunised groups. Non-specific stimulation of T lymphocytes with anti-CD3 antibodies shows similar levels of IFN-γ in the different groups (treated or non-treated with BCG) suggesting that immunisation with BCG does not modify the number of T lymphocytes present in the lungs (FIG. 9B).

The results presented in FIG. 21 show also a statistically significant (p<0.001) higher level of IL-10 in the extended freeze-dried killed BCG treated groups compared to living BCG and heat-inactivated BCG treated groups.

The differences of the cytokines expression profile in the lungs between the extended freeze-dried killed BCG treated groups and the groups treated with the other BCG preparations indicate that extended freeze-dried killed BCG activity is correlated with modifications in the leukocyte populations present in the lung tissues after allergen delivery. The high amount of IL-10 and low amount of INF-γ released by lung explants could assert the presence of regulatory cells in lung tissues of the extended freeze-dried killed BCG groups, after allergen delivery.

e) Level of Anti-OVA Specific IgE

Figure 10:
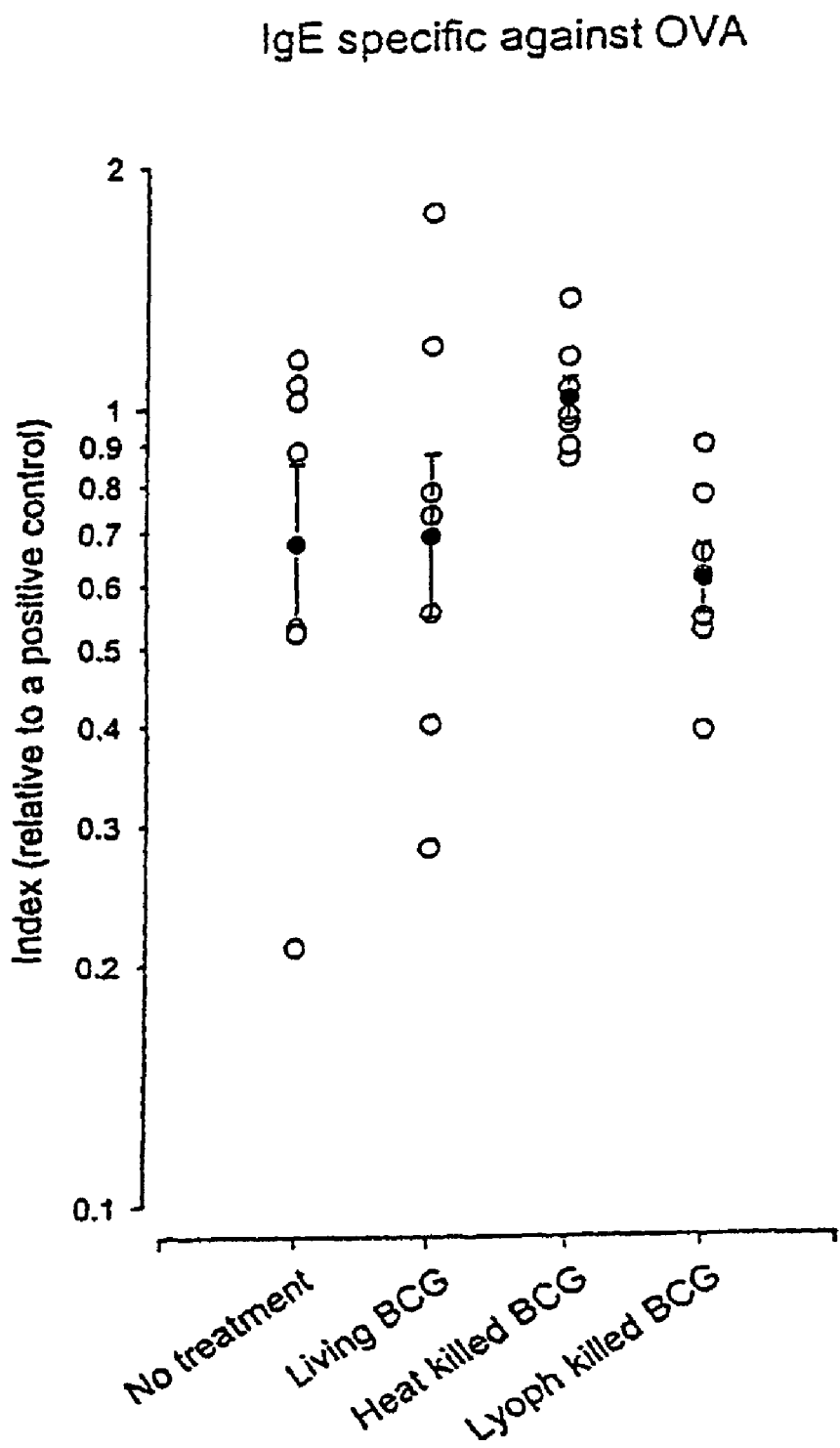
FIG. 10 illustrates the level of OVA-specific IgE in the serum of mice that have been treated in a curative protocol with living BCG, heat-killed BCG, extended freeze-dried killed BCG (Lyoph killed BCG) or non-treated. Individual data (-○-) and mean±SEM per group of mice (-●-) are presented.

The immunization with OVA having been realized before treating with the different BCG preparations (curative protocol), the level of anti-OVA IgE is identical for all the groups (FIG. 10), suggesting that the protective effect observed with extended freeze-dried killed BCG does not involve a direct effect on IgE concentration.

EXAMPLE 4

Analysis of the Cytokines Produced by Alveolar Macrophages Stimulated by Heat-Killed or Extended Freeze-Dried Killed BCG 1) Material and Methods BP2 and BALB/c mice ($H-2^d$) mice, obtained and maintained as mentioned in example 3, were immunized with OVA as described in example 3b. One week after the last injection with OVA, mice were anesthetised by the intraperitoneal route with a lethal dose of urethane (1.5 g/kg; SIGMA). Circulating blood was removed from the abdominal aorte and a canula connected to a syringe was placed in the trachea, and the lungs were washed twice with 0.5 ml and 5 times with 1 ml of HBSS medium (Life Technologies) containing 2% of foetal calf serum. The number of macrophages present in the BAL was determined in an automatic counting equipment (ZBI), provided by COULTER. The macrophages were centrifuged at 1000 rpm for 20 min at room temperature and their concentration was adjusted to 340. $10^3$ cells/ml in RPMI 1640 medium containing 3% fetal calf serum, 2 mM glutamine, 100 UI/ml penicillins and 10 μg/ml streptomycine. The macrophages were then distributed in a 96 well plate for tissue-culture (100 000 cells/well) and incubated for at least 2 hours at 37° C. in the presence of 5% $CO_2$. After, removal of the non-adherent cells by several washes with RPMI medium, macrophages were cultured in the presence of the heat-killed BCG or extended freeze-dried killed BCG (5 equivalent CFU per macrophage e.g. 1.6 $10^6$ CFU/ml for both BCG preparations); *E. coli* lipopolysaccharide (LPS; 1 μl/ml) and OVA (10 μg/ml) were used as controls. The cell culture supernatant were harvested 2, 4, 6, 8, 12, 24, 48, 72 and 96 hours after addition of the different preparations and frozen immediately at −20° C.

2) Results

Figure 11:
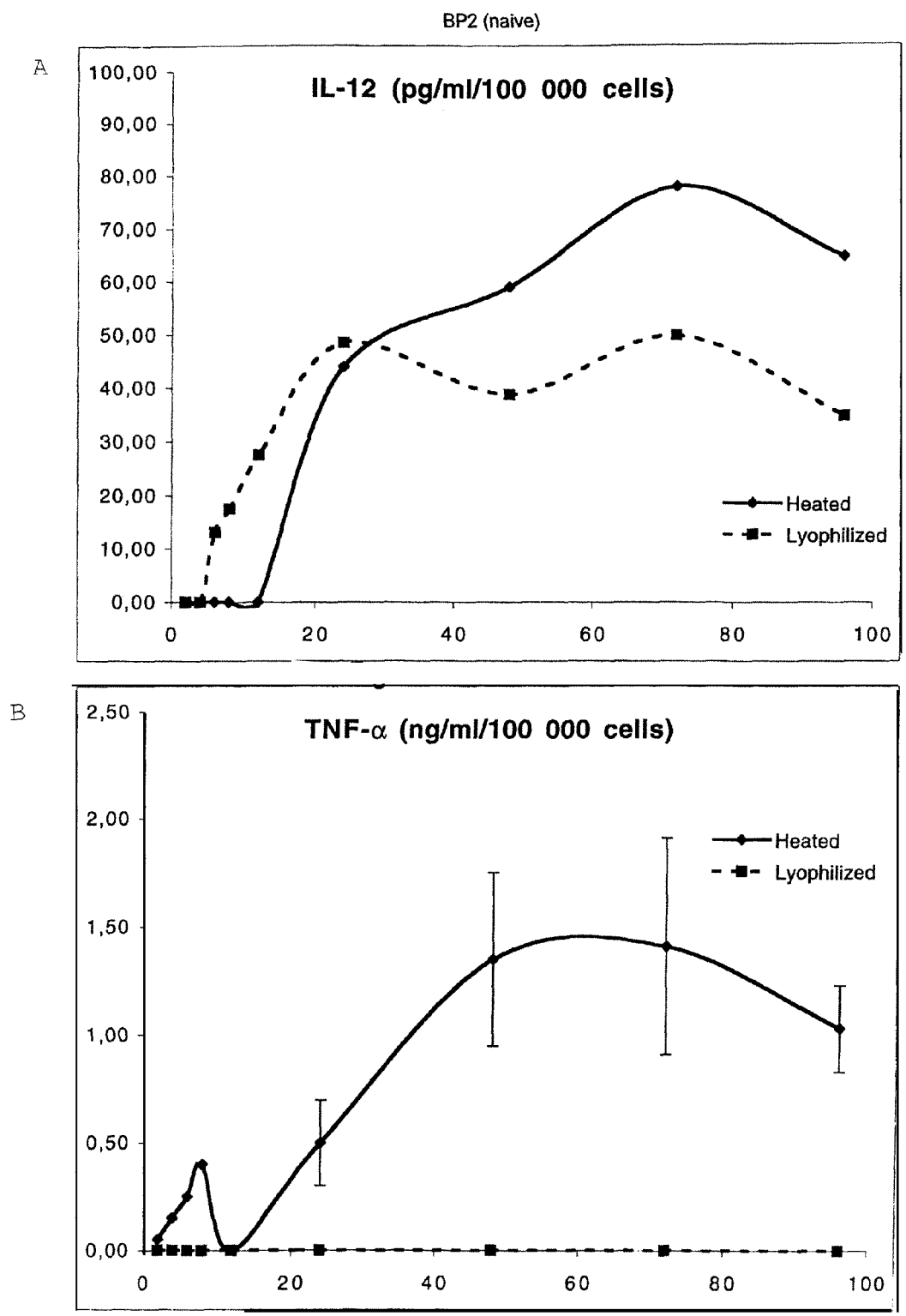
FIGS. 11A and 12A illustrate the production of IL-12 (p70 and p40) by alveolar macrophages from respectively BP2 and BALB/c mice immunised with OVA, that have been stimulated in vitro by either heat-killed BCG (Heated) (-567-), or extended freeze-dried killed BCG (Lyophilized) (...■...). Data are expressed in µg/ml per 100 000 cells.
Figure 12:
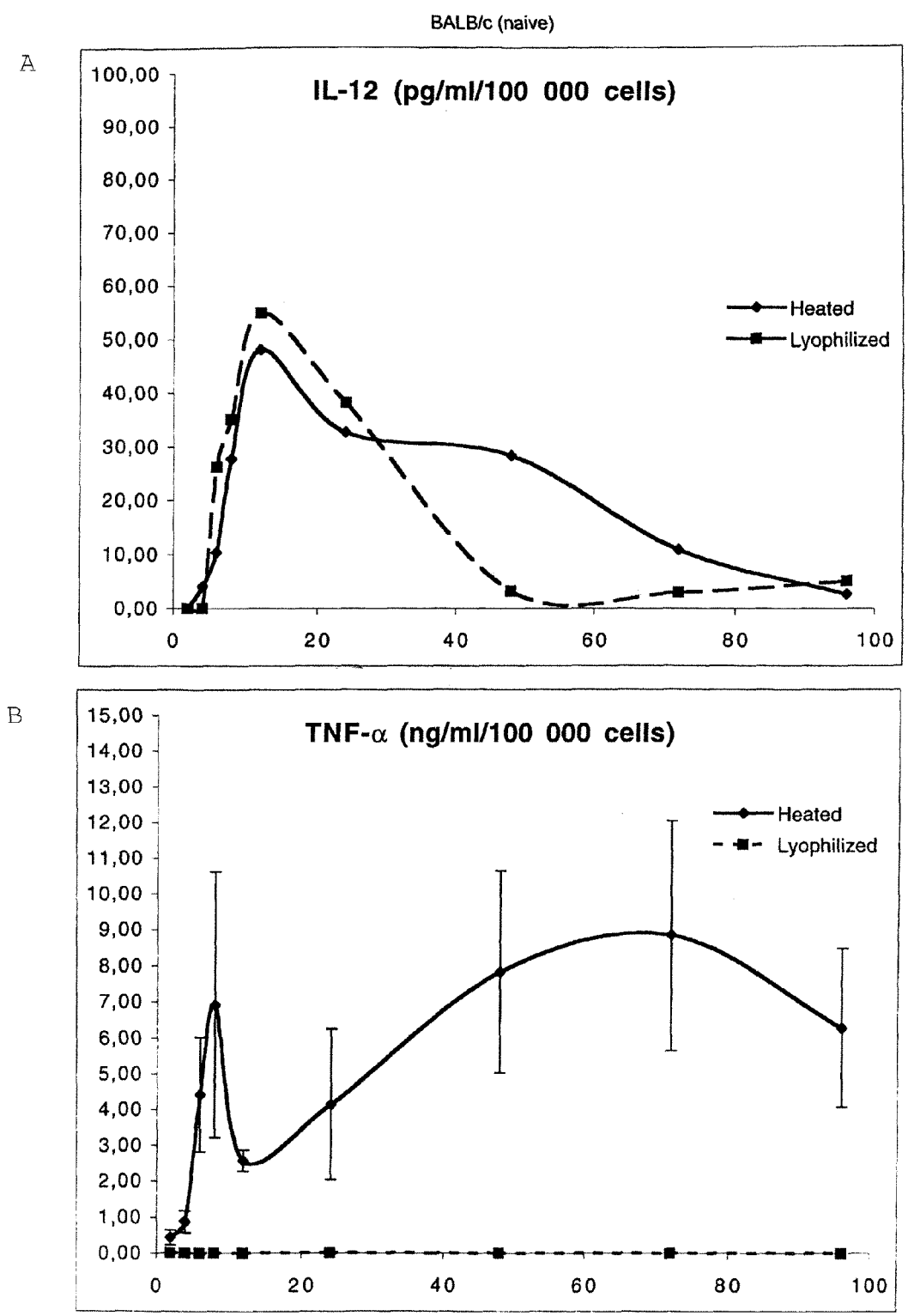

The results presented in FIGS. 11 and 12 show that:

1) IL-12 which is involved in the maturation of the Th1 cells and the production of anti-allergic cytokines (IFN-γ) is produced by BALB/c and BP2 mice alveolar macrophages stimulated by extended freeze-dried killed and heat-killed BCG preparations, 2) TNF-α a cytokine that can be associated with important inflammatory side-effects (necrosis, ulceration . . . ) is produced only by BALB/c and BP2 mice alveolar macrophages stimulated by heat-killed BCG preparations; no TNF-α is produced by alveolar macrophages stimulated by extended freeze-dried killed BCG preparations at the concentrations used in the present experiments.

These results support the minimal adverse effects observed after extended freeze-dried BCG injection, contrary to the side effects observed after heat-killed and living BCG injection.

EXAMPLE 5

The Administration of Extended Freeze-Dried Killed BCG does not Induce Delayed Type Hypersensitivity (DTH) to BCG Purified Proteins Derivatives (PPD)

1) Materials and Methods

Mice were immunised with OVA and treated with different preparations of BCG, or non-treated, as described in example 3d. 100 days after the first subcutaneous injection with the different BCG preparations, the delayed type hyper-sensitivity (DTH) to BCG purified proteins derivatives (PPD) which is used for the diagnosis of tuberculosis in humans was performed on the different groups of mice. More precisely, 50 µl of PPD in saline (4 µg) was injected into the mice footpad and 24 h later the footpad swelling was measured.

2) Result

The results presented in FIG. 13 show that mice immunised with extended freeze-dried killed BCG (equivalent to $10^7$ CFU or 10 µg) do not develop a delayed type hypersensitivity to BCG purified proteins derivatives as shown by a negative skin-test. The mice developed a small sensitization against PPD only after injection of large dose of extended freeze-dried killed BCG (1 mg and 10 mg). By comparison, mice immunised with living BCG or heat-killed BCG, even at low doses ($10^7$ CFU of living BCG or equivalent to $10^8$ bacterial corpses for heat-inactivated BCG) develop a delayed type hypersensitivity to BCG purified proteins derivatives as shown by a positive skin-test. These results are correlated with the preceding results (FIGS. 9 and 21) showing a small production of IFN-γ under specific stimulation, in the extended freeze-dried killed BCG treated groups, contrary to the groups treated with other BCG preparations showing production of higher level of IFN-γ under specific stimulation. Similarly, reactivity of guinea-pigs to PPD is marginal after extended freeze-dried killed BCG treatment.

These results indicate that following immunisation with extended freeze-dried killed BCG, a particular sub-type of specific T lymphocytes are selected or alternatively specific T cells are immobilised in some particular tissues. Consequently, as opposed to immunisation, with living BCG or heat-killed BCG, immunisation with extended freeze-dried killed BCG does not interfere with the diagnosis of tuberculosis by the DTH skin-test.

EXAMPLE 6

Protective Effect of Extended Freeze-Dried (EFD) Killed Mycobacteria on Asthma in a Guinea-Pig Model 1) Material and Methods Male adult guinea-pigs (350 g) were immunized by the subcutaneous route with 10 µg ovalbumin (OVA; ICN Laboratories) and 1 mg alum in saline (0.4 ml final volume).

Three weeks after, said guinea-pigs (3 groups of 10 animals) were injected intradermally with either extended freeze-dried killed BCG ($10^7$ or $10^8$ CFU equivalent i.e. 10 µg or 100 µg), or PBS (control).

The broncho-pulmonary reactivity is assayed on guinea-pigs with a method different to that used for mice; the sensitivity of each animal was evaluated with increasing doses of aerosolized histamine (20, 50, 100 or 400 µg), 24 h before allergen challenge, and the highest concentration of histamine giving elevated Penh values was considered to be the basal level of sensitivity to histamine A similar measure was performed 24 h after the allergen challenge; OVA immunized guinea pigs develop a higher sensitivity to histamine, less histamine is thus needed to obtain the same Penh values than before the challenge.

More precisely:

Six guinea-pigs of each group have been tested for their broncho-pulmonary reactivity with an histamine test performed 7 to 10 weeks after the injection of BCG or control product (e.g. 10 to 13 weeks after the ovalbumin immunisation).

The dosage of histamine triggering a clear bronchoconstriction is measured, for each guinea-pig, with a barometric plethysmograph.

Each guinea-pig is its own control, knowing that the basal reactivity is determined the $1^{st}$ day of the test.

24 hours after, an ovalbumin aerosol is administered. The $3^{rd}$ day the histamine reactivity is measured again.

The administration of ovalbumin increases the broncho-pulmonary hyper-reactivity to histamine.

2) Results

The results presented in FIG. 14 show that 5/6 and 6/6 guinea-pigs that have been treated respectively with 10 µg ($10^7$ CFU equivalent) (FIG. 14B) or 100 µg ($10^8$ CFU equivalent) (FIG. 14C) extended freeze-dried killed BCG according to the invention, are protected against broncho-pulmonary hyper-reactivity (no increase of the histamine sensitization) whereas in the control group (FIG. 14A) (no treatment with BCG) there is a significant increase of broncho-pulmonary hyper-reactivity to histamine (×4).

EXAMPLE 7

Minimal Side Effects of Extended Freeze-Dried Killed BCG a) No Anemia and No Thrombopenia Mice were injected intravenously with extended freeze-dried killed BCG (10 µg) or the different BCG preparations as described in example 3d, or non-treated. 18 days after the injection, red blood cells and platelets numbers were determined from a blood sample.

The results presented in FIG. 22 show that, contrary to the living BCG and the heat-killed BCG treated groups, no anemia and no thrombopenia were observed in the extended freeze-dried BCG treated group.

b) Minimal Inflammatory Reaction at the Site of Injection

At day 0, the different BCG preparations, as described in example 3d, were injected subcutaneously (in the footpad area) to groups of mice. Living BCG was injected once only and heat-killed and extended freeze-dried killed BCG were injected twice (day 0 and day 36). The foot pad increase was then measured every week for ten weeks.

The results presented in FIG. 23 show that extended freeze-dried killed BCG exhibits minimal inflammatory side effects.

c) Reduced TNF-α Production After LPS Stimulation

Lung explants from mice treated 18 days previously with the different BCG preparations as described above, were maintained in vitro in presence or not of LPS, and TNF-α production was measured by ELISA using commercial kits, according to the manufacturer's instructions. The results presented in FIG. 24 show that, contrary to living BCG and heat-killed BCG treatment, extended freeze-dried killed BCG treatment does not induce the production and/or the activation of macrophages.

EXAMPLE 8

Analysis of the Cells in the Draining Lymph Nodes and in the Spleen after Subcutaneous Injection of Extended Freeze-Dried Killed BCG 1) Material and Methods The cells present in the draining lymph nodes of mice treated 48 hours previously by the subcutaneous route, with the different BCG preparations as described in example 3d, were analysed by flow cytometry using monoclonal antibodies directed to cell surface markers of different leukocyte populations, labelled with various fluorochromes.

The cells present in the spleen of mice treated by the subcutaneous route with extended freeze-dried killed BCG, were analysed as above described, after in vitro stimulation in the presence of OVA or BCG culture supernatant or no stimulation.

2) Results
a) Draining Lymph Nodes

The analysis of the cells present in the draining lymph nodes show that by comparison with the living BCG and the heat-killed BCG treated groups, the cells present in the lymph nodes were three to five times more numerous 48 h after subcutaneous injection of extended freeze-dried killed. BCG. A kinetic analysis of the different leukocyte populations for four days after the injection of extended freeze-dried killed BCG, show a transient increase of the dendritic cells ($CD11c^+$) number at 48 hours, as well as an increasing number of B220+ and CD4+ lymphocytes from 6 hours to 96 hours.

b) Spleen

The analysis of the cells present in the spleen show:
a significant increase in the number of $CD11c^+Gr1^+B220^+$ plasmacytoid dendritic cells in the extended freeze dried treated group, no increase of the number of $CD8\alpha^+$ cells was observed in the same group (FIG. 25).
a significant increase in the number of $CD4^+ CD25^+ IL-10^+$ cells in the extended freeze dried treated group, either stimulated in vitro with OVA or BCG culture supernatant or non-stimulated (FIG. 26).

The results show that in the mice model of asthma, extended freeze-dried killed BCG is able to induce a significant increase in the number of cells which induce immunomodulatory cells ($CD11c^+$ $Gr1^+$ $B220^+$ plasmacytoid dendritic cells) or are themselves immunomodulatory cells ($CD4^+$ $CD25^+$ $IL-10^+$ cells) in the mice which have been previously sensitized to an allergen (OVA or water soluble ray grass pollen), which results in a protective effect against the symptoms of asthma.

EXAMPLE 9

Extended Freeze-Dried Killed BCG is Active by the Oral Route

Mice which have been immunized previously with OVA, as described in example 3d were treated orally with 1 mg extended freeze-dried at days 42, 44, 46 and 62, 64 and 66 or non-treated and then challenged or not with OVA at day 96. The protective effect of extended freeze-dried killed BCG was assessed by numeration of lungs cells infiltrate as described in example 3.

The results show a significant decrease $p<0.001$ of the total cell number in the lungs of the extended freeze-dried killed BCG treated group, by comparison with the untreated group (FIG. 27). Analysis of the leukocyte populations show a significant decrease of the macrophages, polynuclears and dendritic cells numbers in the lungs of the treated group.

EXAMPLE 10

Determination of the Active Dose, the Rhythm of Administration, The Duration and the Delay of Action of Extended Freeze-Dried Killed BCG Extended freeze-dried killed BCG was injected by the subcutaneous route to mice previously immunized and then challenged with OVA, and its activity was then tested as described in example 3.

a) Active Dose and Dose Number

Adult mice were sensitized with OVA at days 0 and 7, injected by the subcutaneous route with extended freeze-dried killed BCG once at day 45 or twice at days 45 and 65, and then challenged with ovalbumin at day 96. The activity of extended freeze-dried killed BCG was tested by the prevention of bronchopulmonary hyper-reactivity in the BP2 model of asthma as described in example 3.

The smallest dose (10 µg) was active and doses larger than 100 µg did not increase the activity.

A protective effect was observed with one dose (10 µg) of extended freeze-dried killed BCG only (FIG. 28).

b) Delay of Action of Extended Freeze-Dried Killed BCG

In order to determine the time sequence to obtain the extended freeze-dried killed BCG efficacy, adult mice (6 per group) were sensitized with OVA at days 0 and 7, injected subcutaneously with 100 µg extended freeze-dried killed BCG at day 14 and then challenged with OVA at day 21, 28 or 35. The activity of extended freeze-dried killed BCG was tested by the prevention of bronchopulmonary hyper-reactivity in the BP2 model of asthma as described in example 3.

The prevention of bronchopulmonary hyper-reactivity occurs only if a delay of two to three weeks is present between extended freeze-dried killed BCG administration and challenge (FIG. 29); this result indicates that the recruitment and expansion of a given cell population is required before extended freeze-dried killed BCG is active. This result confirms also that one dose of extended freeze-dried killed BCG is sufficient to protect the mice against asthma.

c) Duration of Action of Extended Freeze-Dried Killed BCG

In order to determine the duration of action of extended freeze-dried killed BCG, adult mice (6 per group) were sensitized with OVA at days 0 and 7, injected subcutaneously with 100 µg extended freeze-dried killed BCG at day 45 and 65 and then challenged with OVA at day 96 or 42. The activity of extended freeze-dried killed BCG was assessed by the preventive effect on bronchopulmonary hyper-reactivity and by numeration of the lungs cell infiltrate, in the BP2 model of asthma, as described in example 3.

The results show that the extended freeze-dried killed BCG protective effect persists at least for two months (FIG. 30).

d) Preventive Versus Curative Protocol of Administration of Extended Freeze-Dried BCG.

The previous results as presented above, demonstrate the efficacy of extended freeze-dried killed BCG in a "curative protocol" (administration after allergen immunization). Thus, in order to evaluate the efficacy of extended freeze-dried killed BCG in a preventive protocol, mice were treated as follows:

adult mice (6 to 7 weeks old; 6 mice per group) were injected subcutaneously with extended freeze-dried killed BCG (100 μg) at days 14, 21 or 28 before OVA immunization (days-14, -21 and -28), immunized with OVA at days 0 and 7 and then challenged with OVA at day 14.

newborn mice (7 to 8 days old, 6 to 8 mice per group) were injected subcutaneously or intranasally with extended freeze-dried killed BCG (100 μg) at day 56 before OVA immunization (day-56), immunized with OVA at days 0 and 7 and then challenged with OVA at day 14.

The activity of extended freeze-dried killed BCG in the preventive protocol was assessed by the preventive effect on broncho-pulmonary hyper-reactivity in the BP2 model of asthma, as described in example 3.

The results in adult mice show a protective effect of extended freeze-dried BCG in a preventive protocol, only when the preparation is injected some days before sensitization (2 weeks and 3 weeks).

The results in newborn mice show a protective effect of extended freeze-dried BCG in a preventive protocol, only with the subcutaneous administration; the intranasal route is poorly active in these conditions.

The invention claimed is:

1. A method of treating autoimmune diseases and allergy, the method comprising administering to a patient in need of such treatment, an amount effective to induce modulation of an immune response against a self antigen or an allergen of at least one of a bacterial preparation consisting of killed non-denatured *Mycobacterium bovis* BCG cells and less than 1.5% of residual water;

a pharmaceutical composition, comprising (1) a bacterial preparation consisting of killed non-denatured *Mycobacterium bovis* BCG cells and less than 1.5% of residual water or at least one fraction thereof with less than 0.5% residual water, and (2) one or more of a pharmaceutically acceptable carrier, an additive, an immunostimulant, an adjuvant and an immunomodulator distinct from the bacterial preparation, wherein the pharmaceutical composition does not comprise any living bacteria and comprises less than 0.5% residual water; and a bacterial preparation comprising killed non-denatured *Mycobacterium bovis* BCG cells and less than 0.5% residual water, which is prepared by a process comprising harvesting a culture of live bacteria cells, freezing the bacteria cells in water or in an aqueous solution of salt, killing the frozen bacteria cells by drying them in a lyophilise, for a time sufficient to remove at least 99.5% of the water, and collecting the freeze-dried killed bacteria cells, wherein the bacterial preparation does not comprise any living bacteria.

2. The method according to claim 1, comprising administering an amount effective to induce modulation of the immune response against a self antigen or an allergen of a bacterial preparation consisting of killed non-denatured *Mycobacterium bovis* BCG cells and less than 1.5% of residual water.

3. The method according to claim 1, wherein the *Mycobacterium bovis* BCG cells are freeze dried killed bacteria obtainable by a freeze-drying process.

4. The method according to claim 1, wherein the bacterial preparation is prepared by a freeze-drying process, comprising: (i) harvesting a culture of live bacteria cells, (ii) washing the bacteria cells in water, (iii) freezing the bacteria cells in water, (iv) killing the frozen bacteria cells by drying them in a lyophiliser, for a time sufficient to remove at least 98.5% of the water, and (v) collecting the freeze-dried killed bacteria cells.

5. The method according to claim 1, wherein the bacterial preparation is prepared by a freeze-drying process comprising harvesting a culture of live bacteria cells, freezing the bacteria cells in water, killing the frozen bacteria cells by drying them in a lyophiliser, for a time sufficient to remove at least 98.5% of the water, and collecting the freeze-dried killed bacteria cells.

6. The method according to claim 1, wherein killing the frozen bacteria cells by drying in a lyophilizer is performed at a drying chamber pressure of about 0.02 mBar to 0.2 mBar.

7. The method according to claim 1, wherein the amount of residual water in the bacterial preparation is less than 1%.

8. The method according to claim 1, wherein the amount of residual water in the bacterial preparation is less than 0.5%.

9. The method according to claim 1, comprising administering an amount effective to induce modulation of the immune response against a self antigen or an allergen of a pharmaceutical composition, comprising (1) a bacterial preparation consisting of killed non-denatured *Mycobacterium bovis* BCG cells and less than 1.5% of residual water or at least one fraction thereof with less than 0.5% residual water, and (2) one or more of a pharmaceutically acceptable carrier, an additive, an immunostimulant, an adjuvant and an immunomodulator distinct from the bacterial preparation, wherein the pharmaceutical composition does not comprise any living bacteria and comprises less than 0.5% residual water.

10. The method according to claim 1, comprising administering an amount effective to induce modulation of the immune response against a self antigen or an allergen of a bacterial preparation comprising killed non-denatured *Mycobacterium bovis* BCG cells and less than 0.5% residual water, which is prepared by a process comprising harvesting a culture of live bacteria cells, freezing the bacteria cells in water or in an aqueous solution of a salt, killing the frozen bacteria cells by drying them in a lyophiliser, for a time sufficient to remove at least 99.5% of the water, and collecting the freeze-dried killed bacteria cells, wherein the bacterial preparation does not comprise any living bacteria.

11. The method according to claim 1, wherein said disease comprising an immune dysregulation is an autoimmune disease and is selected from the group consisting of multiple sclerosis, rheumatoid arthritis, Crohn disease and diabetes mellitus.

12. The method according to claim 1, wherein said disease comprising an immune dysregulation is allergy and is selected from the group consisting of asthma, allergic rhinitis, conjunctivitis and atopic dermatitis.

13. The method according to claim 1, wherein the bacterial preparation is administered orally, sublingually, parenterally, subcutaneously or intranasally.

14. The method according to claim 1, wherein the patient is human.

15. The method according to claim 14, wherein the patient is a human baby.

* * * * *